(12) United States Patent
Sørensen et al.

(10) Patent No.: US 9,683,224 B2
(45) Date of Patent: Jun. 20, 2017

(54) ENZYMES

(75) Inventors: Jens Frisbæk Sørensen, Århus N (DK); Lone Brønd Miller, Viby J (DK)

(73) Assignee: DuPont Nutrition Biosciences ApS, Copenhagen (DK)

( * ) Notice: Subject to any disclaimer, the term of this patent is extended or adjusted under 35 U.S.C. 154(b) by 0 days.

(21) Appl. No.: 14/344,508

(22) PCT Filed: Sep. 14, 2012

(86) PCT No.: PCT/EP2012/068041
§ 371 (c)(1),
(2), (4) Date: Mar. 12, 2014

(87) PCT Pub. No.: WO2013/037933
PCT Pub. Date: Mar. 21, 2013

(65) Prior Publication Data
US 2014/0329283 A1    Nov. 6, 2014

Related U.S. Application Data

(60) Provisional application No. 61/534,574, filed on Sep. 14, 2011, provisional application No. 61/676,535, filed on Jul. 27, 2012.

(30) Foreign Application Priority Data

Sep. 14, 2011 (EP) .................................... 11181241

(51) Int. Cl.
| | | |
|---|---|---|
| C12C 1/00 | (2006.01) | |
| C12P 7/18 | (2006.01) | |
| C12P 7/06 | (2006.01) | |
| C12N 9/42 | (2006.01) | |
| C12N 9/14 | (2006.01) | |
| C12N 9/24 | (2006.01) | |
| C12N 9/26 | (2006.01) | |
| C12C 11/00 | (2006.01) | |
| D21F 11/00 | (2006.01) | |
| C07H 21/04 | (2006.01) | |
| C07K 1/00 | (2006.01) | |
| C12N 9/30 | (2006.01) | |
| C12C 12/00 | (2006.01) | |
| D21H 17/00 | (2006.01) | |
| A23L 5/20 | (2016.01) | |

(52) U.S. Cl.
CPC .............. *C12N 9/2482* (2013.01); *A23L 5/25* (2016.08); *C12C 11/003* (2013.01); *C12C 12/002* (2013.01); *C12N 9/24* (2013.01); *C12N 9/242* (2013.01); *C12N 9/244* (2013.01); *C12N 9/2408* (2013.01); *C12P 7/06* (2013.01); *C12Y 302/01006* (2013.01); *C12Y 302/01008* (2013.01); *C12Y 302/01014* (2013.01); *D21H 17/005* (2013.01); *Y02E 50/17* (2013.01)

(58) Field of Classification Search
CPC .... C12N 9/242; C12N 9/2408; C12N 9/2482; C12N 9/244; C12N 9/24; C12Y 302/01014; C12Y 302/01008; C12Y 302/01006; Y02E 50/17; C12C 11/003; C12C 12/002; C12P 7/06; D21H 17/005
USPC ......... 435/93, 158, 161, 209, 195, 200, 201; 426/16; 162/158; 536/23.2; 530/350
See application file for complete search history.

(56) References Cited

U.S. PATENT DOCUMENTS

| | | | |
|---|---|---|---|
| 5,470,725 A | 11/1995 | Borriss et al. | |
| 5,610,046 A | 3/1997 | van Ooyen et al. | |
| 6,103,511 A * | 8/2000 | Li et al. ........................ | 435/209 |
| 7,960,148 B2 * | 6/2011 | Steer ...................... | A23K 1/002 |
| | | | 424/439 |
| 8,043,839 B2 * | 10/2011 | Weiner et al. ................ | 435/200 |
| 2008/0233175 A1 | 9/2008 | Steer et al. | |

FOREIGN PATENT DOCUMENTS

| | | |
|---|---|---|
| WO | WO94/14953 | 7/1994 |
| WO | WO94/21785 | 9/1994 |
| WO | WO95/31533 | 11/1995 |
| WO | WO97/13853 | 4/1997 |
| WO | WO97/42301 | 11/1997 |
| WO | WO98/05788 | 2/1998 |
| WO | WO98/28410 | 7/1998 |
| WO | WO99/57325 | 11/1999 |
| WO | WO2004/087889 | 10/2004 |
| WO | WO2005/003319 | 1/2005 |
| WO | WO2005/056744 | 6/2005 |
| WO | WO2005/059084 | 6/2005 |
| WO | WO2005/100852 | 10/2005 |
| WO | WO2005/118769 | 12/2005 |
| WO | WO2006/066582 | 6/2006 |
| WO | WO2006/114095 | 11/2006 |
| WO | WO2007/056321 | 5/2007 |

(Continued)

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*

(Continued)

*Primary Examiner* — Ganapathirama Raghu
(74) *Attorney, Agent, or Firm* — DuPont Nutrition Biosciences ApS

(57) ABSTRACT

The present invention relates to new enzymes with improved properties and to compositions comprising these enzymes suitable for use in the production of a food, feed, or malt beverage product, such as in a brewing process.

9 Claims, 7 Drawing Sheets

(56) References Cited

FOREIGN PATENT DOCUMENTS

Figure 1:
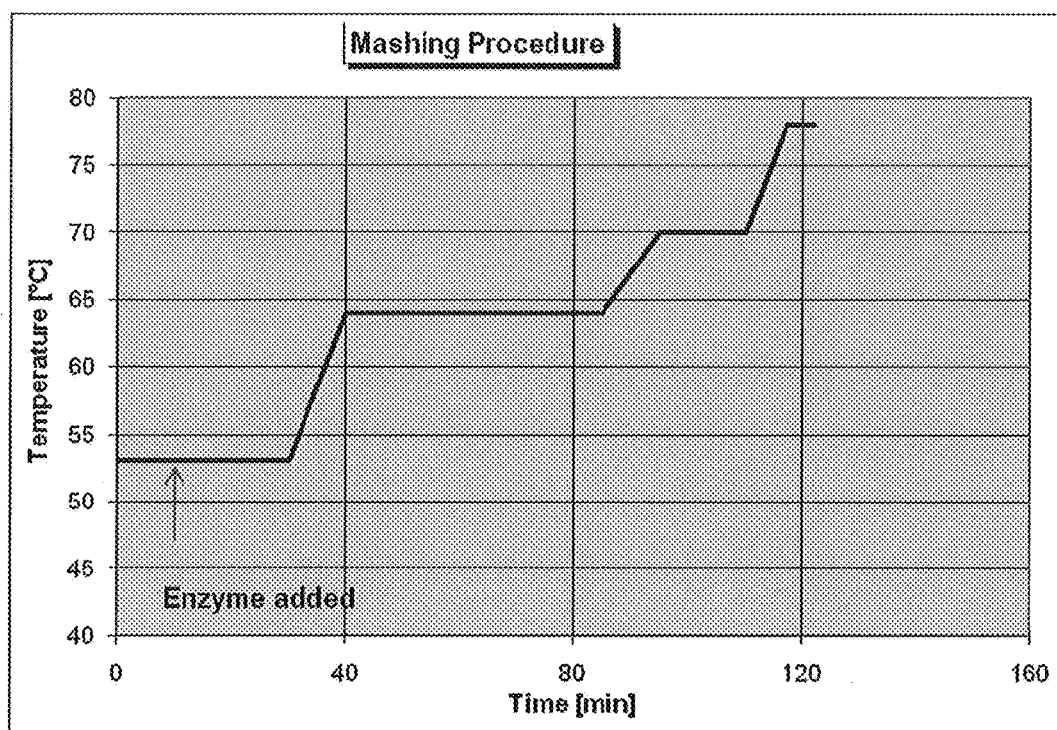

| WO | WO2008/023060 | 2/2008 |
|---|---|---|
| WO | WO2009/108941 | 9/2009 |
| WO | WO2010/059424 | 5/2010 |
| WO | WO2010/072226 | 7/2010 |
| WO | WO2010/128140 | 11/2010 |

OTHER PUBLICATIONS

Murphy et al., The DNA sequence of the gene and genetic control sites for excreted B. subtilis enzyme b-glucanase. Nucleic Acids Res., 1984, vol. 12 (13): 5355-5367.*

Banerjee Goutami et al, "Rapid optimization of enzyme mixtures for deconstruction of dicerse pretreatment/biomass feedstock combinations," Biotechnology for Biofuels (2010), vol. 3, No. 1, p. 22, Biomed Central Ltd, London, UK.

Bunzel et al, "Diferulates as structural components in soluble and insoluble cereal dietary fibre," Journal of the Science of Food and Argiculture (2001), vol. 81, p. 653-60.

Graaff et al, "Regulation of the xylanase-encoding xlnA gene of Aspergillus tubigensis," Molecular Microbiology (1994), vol. 12, No. 3, p. 479-490.

Henrissat, B., "A classification of glycosyl hydrolases based on amino acid sequence similarities," Biochem. J. (1991), vol. 280, pp. 309-316.

International Search Report and Written Opinion dated Apr. 9, 2013, for corresponding PCT Application No. PCT/EP2012/0268041.

Ito et al, "Cloning and sequencing of the xyna gene encoding xylanase a of aspergillus-kawachii," Bioscience Biotechnology Biochemistry (1992), vol. 56, No. 6, pp. 906-912, Japan Society for Bioscience, Biotechnology, and Agrochemistry, Tokyo, JP.

Junqing Wang et al, "Cloning and sequence analysis of a novel xylanase gene, Auxyn10A, from Aspergillus usamii," Biotechnology Letters (2011), vol. 33, No. 5, pp. 1029-1038.

Kvesitadze et al, "Thermostable endo-neta-1, 4-glucanase and endo-bata-1,4-xylanse activity in culture filtrates and a purified enzyme fraction in the thermophilic fungus allescheria terrestris," Microbios (1994), vol. 8, No. 323, pp. 115-123 Cambridge, GB.

Rouau, X. and Surget, A., "A rapid semi-automated method for the determination of total and water-extractable pentosans in wheat flour," Carbohydrate Polymers (1994), 24, 123-132.

Wolf et al,"Genese Encoding xylan and beta-glucan hydrolyzing enzymes in bacillus subtilis: characterization mapping and construction of strains deficient in lichenase, cellulose and xylanse," Microbiology (1995), vol. 141, No. 2, pp. 281-290, Society for General Microbiology, Reading, GB.

First Office Action dated Feb. 28, 2015, issued in Chinese Patent Application No. 201280044661.3, filed Sep. 14, 2012.

Database: Uniprot, Accession No. P04957, "RecName: Full=Beta-glucanase; EC=3.2.1.73; AltName: Full=1,3-1,4-beta-D-glucan 4-glucanohydrolase; AltName: Full=Endo-beta-1,3-1,4 glucanase; AltName: Full=Lichenase; Flags: Precursor;", XP002694418, retrieved from "http://www.genome.jp/dbget-bin/www_bget?uniprot:P04957"; UniProtKB/Swiss-Prot Sequence Entry Date: Aug. 13, 1987.

* cited by examiner

ENZYMES

CROSS REFERENCE TO RELATED APPLICATIONS

This application claims priority to International Patent Application No. PCT/EP2012/068041, filed Sep. 14, 2012 and EP Patent Application No. 11181241.8, filed Sep. 14, 2011 and U.S. Patent Application No. 61/534,574, filed Sep. 14, 2011 and U.S. Patent Application No. 61/676,535 filed Jul. 27, 2012, .The entire disclosures of the foregoing applications are hereby incorporated by reference thereto in their entireties for all purposes.

FIELD OF THE INVENTION

The present invention relates to enzymes with improved properties and to compositions comprising these enzymes suitable for use in the production of a food, beverage (e.g. beer), feed, or biofuel, such as in a brewing process.

BACKGROUND OF THE INVENTION

The use of enzymes in beer production is well known. Application of enzymes to the mashing step to improve mash filterability and increase extract yield is described in WO 97/42302.

WO2005118769 and WO2005059084 relates to a mashing and filtration step in a process for the production of beer, and to enzymatic compositions for use in such a process.

WO1999057325 relates to strains of *Penicillium funiculosum*, to new enzyme mixtures obtained from it and nucleic sequences thereto.

However, there is a need for improved enzymes as well as combination of enzymes useful in the productions of food and beverage products, such as in the mashing, cooking and filtration steps in the production of an alcoholic beverage, such as beer or whiskey.

OBJECT OF THE INVENTION

It is an object of embodiments of the invention to provide enzymes suitable for the production of food and beverage products, such as in the production of an alcoholic or non-alcoholic beverage, such as a cereal- or malt-based beverage like beer or whiskey. The enzymes provided may have improved properties in relation to the use in brewing. These wide varieties of improved properties comprise e.g. improved temperature optimums, improved ratio in activity on soluble (WE-AX) to insoluble (WU-AX) arabinoxylan substrates, reduced total pressure built up during lautering and/or filtration steps of a brewing process, as well as increased filterability of enzyme treated material.

SUMMARY OF THE INVENTION

It has been found by the present inventor(s) that one or more enzyme as well as certain combinations of enzymes have improved properties relative to known enzymes and enzyme combinations, particularly in relation to the use in a process of brewing, wherein starch containing material is treated with the one or more enzyme to produce a brewing mash.

So, in a first aspect the present invention relates to an enzyme exhibiting endo-1,4-β-xylanase activity, which enzyme comprises an amino acid sequence having at least 80% identity with any one selected from SEQ ID NO:1, SEQ ID NO:2, SEQ ID NO:3, SEQ ID NO:4, SEQ ID NO:5, SEQ ID NO:6, SEQ ID NO:17, and SEQ ID NO:18, or any functional fragment thereof.

As used herein "functional fragment" refers to a truncated version of an enzyme with essentially the same or at least a significant degree of enzyme activity as the non-truncated reference enzyme.

In a second aspect, the present invention relates to an enzyme exhibiting endo-1,3(4)-13-1.5 glucanase activity, which enzyme comprises an amino acid sequence having at least 80% identity with any one selected from SEQ ID NO:7, SEQ ID NO:8, SEQ ID NO:9, SEQ ID NO:10, and SEQ ID NO:11, SEQ ID NO:12, SEQ ID NO:13, SEQ ID NO:14, SEQ ID NO:15, SEQ ID NO:16, or any functional fragment thereof.

In a third aspect the present invention relates to a DNA construct comprising a DNA sequence encoding an enzyme according to the invention.

In a further aspect the present invention relates to a recombinant expression vector comprising a DNA construct comprising a DNA sequence encoding an enzyme according to the invention.

In a further aspect the present invention relates to a cell that has been transformed with a DNA construct comprising a DNA sequence encoding an enzyme according to the invention.

In a further aspect the present invention relates to preparation comprising an enzyme, or a DNA construct, or a vector, or a cell according to the invention.

In a further aspect the present Invention relates to composition comprising an enzyme exhibiting endo-1,4-β-xylanase activity according to the invention in combination with any one or more β-glucanase.

In a further aspect the present invention relates to a composition comprising an enzyme exhibiting endo-1,3(4)-β-glucanase activity according to the invention in combination with any one or more xylanase.

In a further aspect the present invention relates to the use of an enzyme according to the invention, or a preparation according to the invention, or a composition according to the invention in the production of a food, feed, or malt beverage product, such as beer or whiskey.

In a further aspect the present invention relates to the use of an enzyme according to the invention, or a preparation according to the invention, or a composition according to the invention, in the production of dough or baked products.

In a further aspect the present invention relates to the use of an enzyme according to the invention, or a preparation according to the invention, or a composition according to the invention, in the preparation of pulp or paper.

In a further aspect the present invention relates to the use of an enzyme according to the invention, or a preparation according to the invention, or a composition according to the invention, for the preparation of cereal components. In some embodiments the cereal is rye, wheat, or barley.

In a further aspect the present invention relates to the use of enzyme according to the invention, or a preparation according to the invention, or a composition according to the invention, in the production of beer or modification of by-products from a brewing process.

In a further aspect the present invention relates to the use of enzyme according to the invention, or a preparation according to the invention, or a composition according to the invention, in the production of wine or juice.

In a further aspect the present invention relates to the use of enzyme according to the invention, or a preparation according to the invention, or a composition according to the invention, in the production of a first- or second-generation biofuel, such as bioethanol.

In a further aspect the present Invention relates to a method of altering filterability of a starch comprising material, said method comprising the step of treating said starch comprising material with enzyme, or a preparation, or a composition according to the invention.

In a further aspect the present invention relates to a method of reducing pressure built up during lautering in a brewing application, said method comprising the step of treating a brewing mash with enzyme, or a preparation, or a composition according to the invention.

In a further aspect the present invention relates to a method for the production of a food, feed, or beverage product, such as an alcoholic or non-alcoholic beverage, such as a cereal- or malt-based beverage like beer or whiskey, said method comprising the step of treating a starch comprising material with enzyme, or a preparation, or a composition according to the invention.

In a further aspect the present invention relates to a method for the production of a brewing mash, said method comprising the step of treating a starch comprising material with an enzyme, or a preparation, or a composition according to the invention.

In a further aspect the present invention relates to a method for the production of a first- or second-generation biofuel, such as bioethanol, said method comprising the step of treating a starch comprising material with an enzyme, or a preparation, or a composition according to the invention.

In a further aspect the present invention relates to a product obtained by a method according to the invention.

In a further aspect the present invention relates to a composition comprising the product obtained by a method according to the invention, such as wherein the product is in a range of 0.1%-99.9%.

LEGENDS TO THE FIGURE

FIG. 1: Mashing profile used in lab scale and pilot scale brewing. Mashing was initiated by a 10 min mashing-in period after which the enzyme was added.

Figure 2:
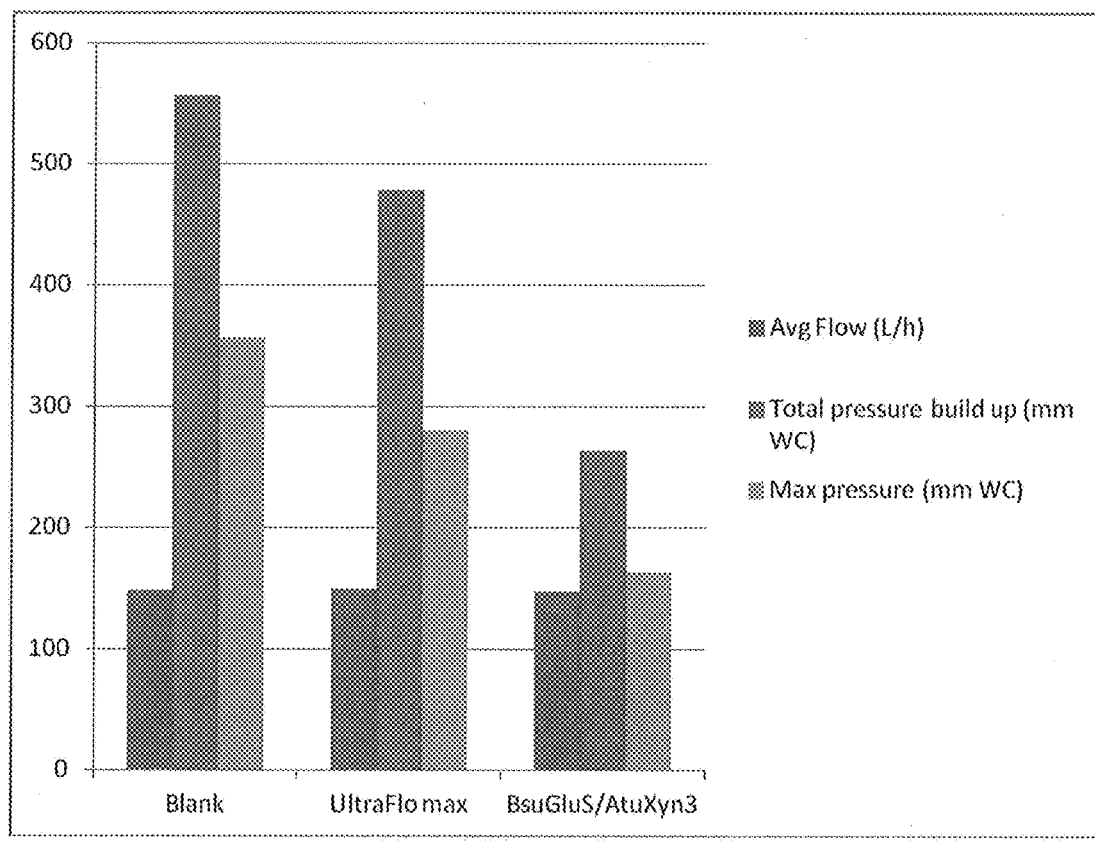

FIG. 2: Pilot scale Brewing application results from verification of the glucanase and xylanases screening. The B: sub glucanase S combined with the A. tub xylanases was tested against a blank and UltraFlo max. Data collected was the average flow (L/h), the total pressure build up over the lautering (mm WC, where 1 mm WC=9.80665 Pa) and the max pressure recorded during the lautering (mm WC).

Figure 3:
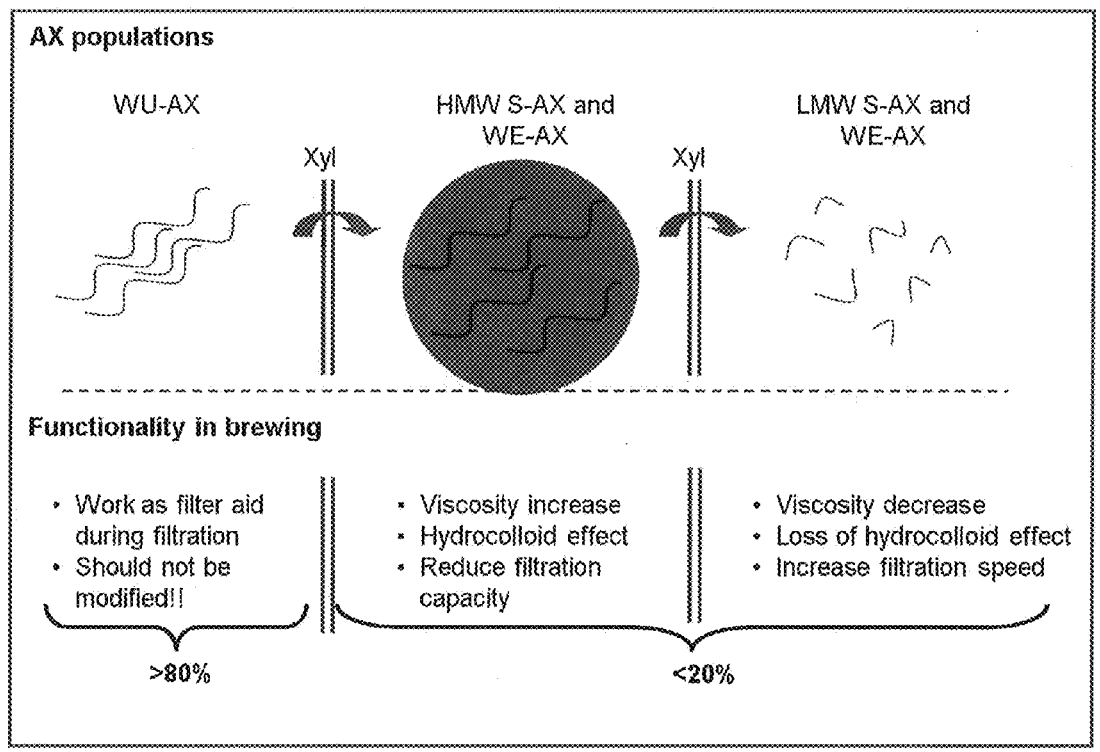

FIG. 3: Xylanase functionality in brewing

Figure 4:
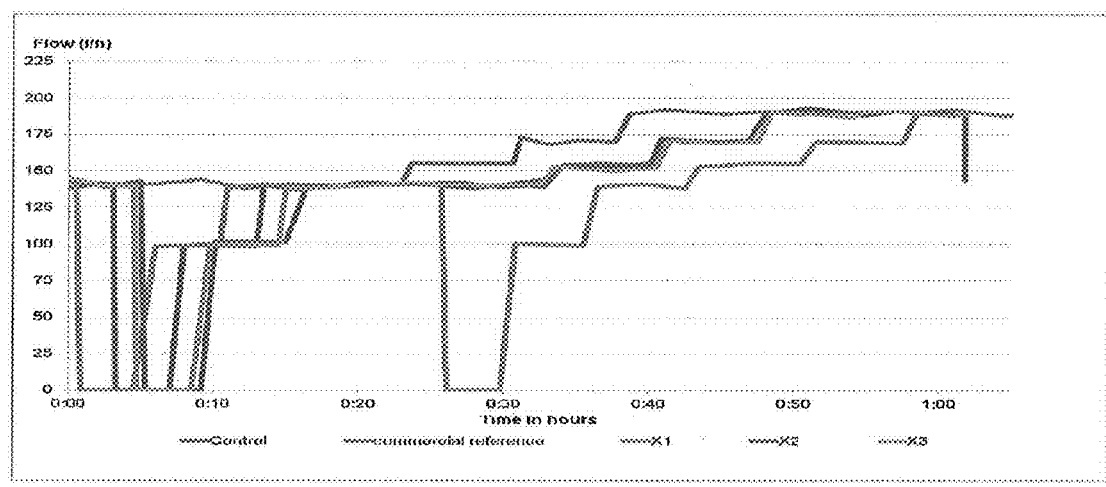

FIG. 4: Flow—lautering applying various xylanase candidates

Figure 5:
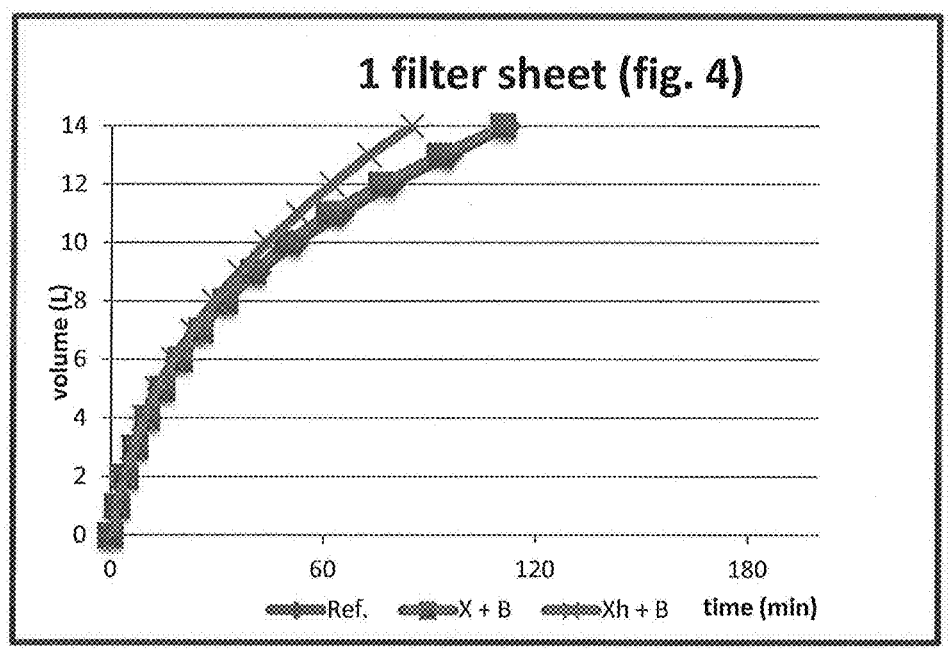

FIG. 5: Beer filtration—average of repeated filtrations

Figure 6:
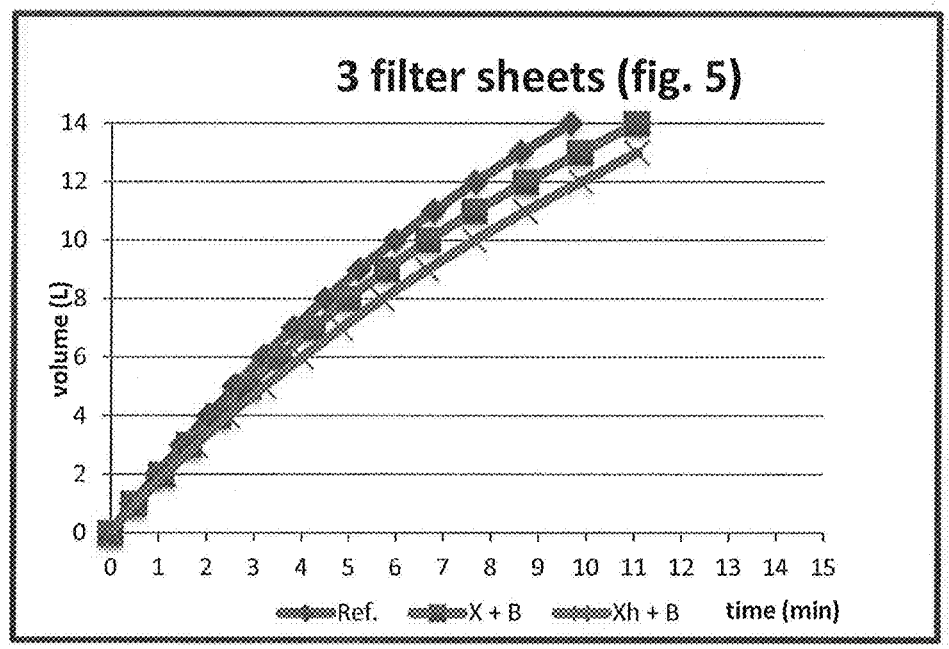

FIG. 6: Beer filtration—average of repeated filtrations

Figure 7:
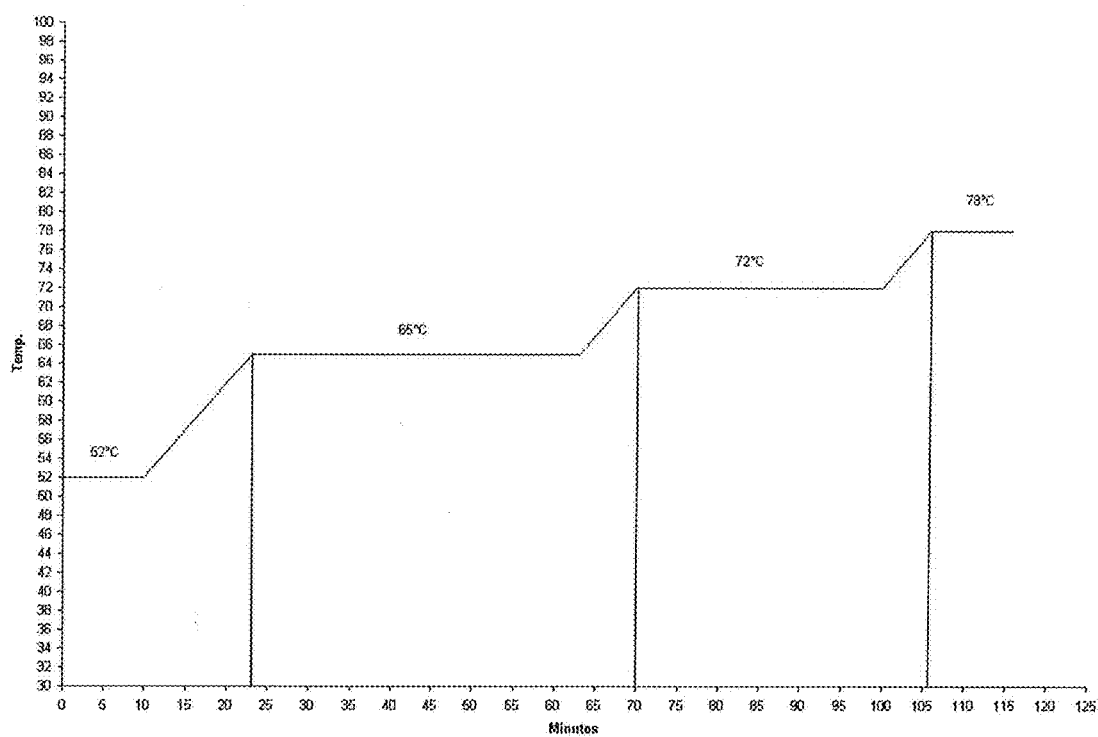

FIG. 7: Mashing diagram of example 3.

DETAILED DISCLOSURE OF THE INVENTION

Beer is traditionally referred to as an alcoholic beverage derived from malt, such as malt derived from barley grain, and optionally adjunct, such as starch containing plant material (e.g. cereal grains) and optionally flavoured, e.g. with hops.

In the context of the present invention, the term "beer" is meant to comprise any fermented wort, produced by fermentation/brewing of a starch-containing plant material, thus in particular also beer produced exclusively from adjunct, or any combination of malt and adjunct.

The term "fermentation" means in the present context production of a substance such as ethanol by growing microorganisms in a culture. Commonly, microorganisms such as yeast are used for fermentation.

As used herein the term "malt" is understood as any malted cereal grain, such as malted barley. "Adjunct" can be defined as any starch-containing plant material which is not malt or barley malt.

"Starch-containing plant material" can e.g. be one or more cereal, such as barley, wheat, maize, rye, sorghum, millet, or rice, and any combination thereof. The starch-containing plant material can be processed, e.g. milled, malted, partially malted or unmalted. Unmalted cereal is also called "raw grain". Examples of non-cereal starch-containing plant material comprise e.g. tubers, such as potatoes and cassava.

As used herein, the terms "beverage" and "beverage(s) product" includes such foam forming fermented beverages as full malted beer, beer brewed under the "Reinheitsgebot", ale, dry beer, near beer, light beer, low alcohol beer, low calorie beer, porter, bock beer, stout, malt liquor, non-alcoholic beer, non-alcoholic malt liquor and the like. The term "beverages" or "beverages product" also includes non-foaming beer and alternative malt beverages such as fruit flavoured malt beverages, e. g., citrus flavoured, such as lemon-, orange-, lime-, or berry-flavoured malt beverages, liquor flavoured malt beverages, e. g., vodka-, rum-, or tequila-flavoured malt liquor, or coffee flavoured malt beverages, such as caffeine-flavoured malt liquor, and the like.

Beer can be made from a variety of starch-containing plant material by essentially the same process, where the starch is consists mainly of glucose homopolymers in which the glucose residues are linked by either alpha-1,4- or alpha-1,6-bonds, with the former predominating.

The process of making fermented beverages such as beer is commonly referred to as brewing. The traditional raw materials used in making these beverages are water, hops and malt. In addition or instead of malt, adjuncts such as common corn grits, refined corn grits, brewer's milled yeast, rice, sorghum, refined corn starch, barley; barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch. The starch will eventually be converted enzymatically into fermentable sugars.

Concerning beers made predominantly from malt (e.g. up to 15-20% adjunct), for a number of reasons, the malt, which is produced principally from selected varieties of barley, has the greatest effect on the overall character and quality of the beer. First, the malt is the primary flavouring agent in beer. Second, the malt provides the major portion of the fermentable sugar. Third, the malt provides the proteins, which will contribute to the body and foam character of the beer. Fourth, the malt provides the necessary enzymatic activity during mashing.

Hops also contribute significantly to beer quality, including flavouring. In particular, hops (or hops constituents) add desirable bittering substances to the beer. In addition, the hops act as protein precipitants, establish preservative agents and aid in foam formation and stabilization. Not all beers are produced using hops. Other stabilizing agents, such as proteases (e.g. papain) may also be used.

Without Wanting to be Construed as Limiting for the Present Invention, a Conventional Brewing Process can be Described as Follows:

The process for making beer is well known in the art, but briefly, it involves five steps: (a) mashing and/or adjunct cooking (b) wort separation and extraction (c) boiling and hopping of wort (d) cooling, fermentation and storage, and (e) maturation, processing and packaging. Typically, in the first step, milled or crushed malt is mixed with water and held for a period of time under controlled temperatures to permit the enzymes present in the malt to convert the starch present in the malt into fermentable sugars.

In the second step, the mash is transferred to a "lauter tun" or mash filter where the liquid is separated from the grain residue. This sweet liquid is called "wort" and the left over grain residue is called "spent grain". The mash is typically subjected to an extraction, which involves adding water to the mash in order to recover the residual soluble extract from the spent grain.

In the third step, the wort is boiled vigorously. This sterilizes the wort and helps to develop the colour, flavour and odour. Hops are added at some point during the boiling.

In the fourth step, the wort is cooled and transferred to a fermentor, which either contains the yeast or to which yeast is added. The yeast converts the sugars by fermentation into alcohol and carbon dioxide gas; at the end of fermentation the fermentor is chilled or the fermentor may be chilled to stop fermentation. The yeast flocculates and is removed.

In the last step, the beer is cooled and stored for a period of time, during which the beer clarifies and its flavour develops, and any material that might impair the appearance, flavour and shelf life of the beer settles out. Prior to packaging, the beer is carbonated and, optionally, filtered and pasteurized.

After fermentation, a beverage is obtained which usually contains from about 2% to about 10% alcohol by weight. The non-fermentable carbohydrates are not converted during fermentation and form the majority of the dissolved solids in the final beer.

This residue remains because of the inability of malt amylases to hydrolyze the alpha-1,6-linkages of the starch. The non-fermentable carbohydrates contribute about 50 calories per 12 ounces of beer.

Recently, there has been a widespread popularization of brewed beverages called light beers, reduced calorie beers or low calorie beers, particularly in the U. S. market. As defined in the U.S., these beers have approximately 30% fewer calories than a manufacturer's "normal" beer.

Further information on conventional brewing processes, as well as definitions for terms used in the field of brewing technology to be applied for the present invention, may be found in "Technology Brewing and Malting" by Wolfgang Kunze of the Research and Teaching Institute of Brewing, Berlin (VLB), 2nd revised Edition 1999, ISBN 3-921690-39-0, 3rd edition (2004): ISBN 3-921690-49-8, $4^{th}$ updated edition, 2010 (ISBN 978-3-921690-64-2).

Xylanases are classified in EC 3.2.1.8, EC 3.2.1.32, EC 3.2.1.136 and EC 3.2.1.156.; their activity may be measured e.g. as described in the examples. Suitable xylanases to be used in combination with an enzyme exhibiting endo-1,3 (4)-β-glucanase activity according to the invention includes any xylanse classified in EC 3.2.1.8, EC 3.2.1.32, EC 3.2.1.136 and EC 3.2.1.156, such as any one disclosed in WO 2010072226, WO 2010072225, WO 2010072224, WO 2005059084, WO2007056321, W02008023060A, WO9421785, WO2006114095, WO2006066582, US 2008233175, and WO10059424.

Endo-1,4-beta xylanase is classified as EC 3.2.1.8. The enzyme causes endohydrolysis of 1,4-beta-D-xylosidic linkages in xylans.

The terms "family 11 xylanase", "Glycoside hydrolase (GH) family 11" or simply "GH 11 xylanase" as used herein refers to an endo-1,4-beta xylanase classified as EC 3.2.1.8, which causes endohydrolysis of 1,4-beta-D-xylosidic linkages in xylans and which is classified as a family 11 xylanase according to B. Henrissat, A classification of glycosyl hydrolases based on amino acid sequence similarities. Biochem. J. 280 (1991), pp. 309-316.

The terms "Family 10 xylanase", "Glycoside hydrolase (GH) family 10", or simply "GH 10 xylanse" comprises enzymes with a number of known activities, such as xylanase (EC:3.2.1.8); endo-1,3-beta-xylanase (EC: 3.2.1.32); cellobiohydrolase (EC:3.2.1.91). These enzymes were formerly known as cellulase family F.

In some embodiments the enzyme exhibiting endo-1,4-β-xylanase activity is a family 11 xylanase. In some embodiments the enzyme exhibiting endo-1,4-β-xylanase activity is a family 10 xylanase.

In one aspect, the enzyme composition according to the invention has endo-1,4-beta xylanase activity as measured by the assay described in the examples.

An assay for measuring xylanase activity may be carried out at pH 3.5 or pH 5 and 50° C. using xylan as substrate, or it can be performed at different pH and temperature values for the additional characterisation and specification of enzymes. Enzyme activity is calculated from the increase in absorbance caused by xylose at 540 nm per unit time.

In some embodiments the enzyme composition according to the invention comprises a xylanase activity of at least about 5000 U/g, such as at least about 6000 (J/g, such as at least about 7000 U/g, such as at least about 8000 U/g, such as at least about 8500 U/g, as measured by in the assay described in the examples.

The enzyme composition according to the invention may have cellulolytic activity. The systematic name of cellulose is 4-(1,3;1,4)-β-D-glucan 4-glucanohydrolase and cellulolytic enzymes or cellulases are classified in EC 3.2.1.4. Cellulase endohydrolyse (1→4)-β-D-glucosidic linkages. in e.g. cellulose, lichenin and cereal β-D-glucans and will also hydrolyse 1,4-linkages in β-D-glucans also containing 1,3-linkages. Cellulase also have other names such as endo-1, 4-β-D-glucanase, β-1,4-glucanase, 3-1,4-endoglucan hydrolase, cellulase A, cellulosin AP, endoglucanase D, alkali cellulose, cellulase A 3, celludextrinase, 9.5 cellulase, avicelase, pancellase SS and 1,4-(1,34,4)-β-D-glucan 4-glucanohydrolase.

In one aspect of the invention, the cellulase activity of the enzyme composition according to the invention is measured by the "Cellulase activity method" as described in the following under the heading "Assays".

In further aspects, the present invention relates to enzymes having endo-'1,3(4)-β-glucanase activity is determined by the assay described in the examples.

"β-glucanase" or "beta-glucanase" as used herein refers to an endo-1,3(4)-beta-glucanase of EC 3.2.1.6. Catalyze the endohydrolysis of (1->3)- or (1->4)-linkages in beta-D-glucans when the glucose residue whose reducing group is involved in the linkage to be hydrolyzed is itself substituted at C-3. Suitable beta-glucanases to be used in combination with an enzyme exhibiting endo-1,4-β-xylanase activity according to the invention includes any one beta-glucanase disclosed in WO2004087889, WO2005059084, WO9414953, WO2007056321, WO9531533, WO08023060, WO2005100582, WO9828410, WO9742301, WO2006066582, WO05118769, WO2005003319, and WO10059424.

The standard assay is carried out at pH 5.0, and it can be performed at different pH values for the additional characterisation and specification of enzymes.

One unit of endo-1,3(4)-β-glucanase activity Is defined as the amount of enzyme which produces 1 μmole glucose equivalents per minute under the conditions of the assay (pH 5.0 (or as specified) and 50° C.).

In some embodiments the enzyme composition according to the invention comprises a 6-glucanase activity of at least about 10000 U/g, such as at least about 12000 U/g, such as at least about 14000 U/g, such as at least about 15000 U/g, such as at least about 18000 U/g as measured by the assay described in the examples.

In further aspects, the enzyme composition according to the invention has laminarinase activity or comprises any one or more further enzyme having laminarinase activity. The laminarinase activity is determined. as described in the laminarase assay described in the Assay section.

Laminarinase may be an endo-1,3(4)-beta-glucanase classified in E.C. 3.2.1.6 or glucan endo-1,3-beta-D-glucosidase classified in E.C. 3.2.1.39. Endo-1,3(4)-beta-glucanase with the alternative names, laminarinase, endo-1,3-beta-glucanase, Endo-1,4-beta-glucanase is classified in E.C. 3.2.1.6. The substrates include laminarin, lichenin and cereal D-glucans and the enzyme catalyse endohydrolysis of (1->3)- or (1->4)-linkages in beta-D-glucans when the glucose residue whose reducing group is involved in the linkage to be hydrolyzed is itself substituted at C-3. Glucan endo-1,3-beta-D-glucosidase with the alternative names (1->3)-beta-glucan endohydrolase, Endo-1,3-beta-glucanase and laminarinase is classified in E.C. 3.2.1.39 and hydrolyse (1->3)-beta-D-glucosidic linkages in (1->3)-beta-D-glucans in substrates as eg. laminarin, paramylon and pachyman.

In some aspects, the enzyme composition according to the invention has arabinanase activity or comprises a further enzyme having arabinanase activity. Arabinanase is classified as EC 3.2.1.99. The systematic name is 5-α-L-arabinan 5-α-L-arabinanohydrolase but it has several other names such as arabinan endo-1,5-α-L-arabinosidase, and endo-1,5-α-L-arabinanase, endo-α-1,5-arabanase, endo-arabanase, 1,5-α-L-arabinan and 1,5-α-L-arabinanohydrolase. Arabinase endohydrolyses (1→5)-α-arabinofuranosidic linkages in (1→5)-arabinans. Arabinanase also acts on arabinan.

In one aspect of the invention, the arabinae activity of the enzyme composition according to the invention is measured by arabinase assay as described in the following under the heading "Assays". The assay can be carried out at pH 3.5 and 50° C. using sugar beet arabinan as substrate, and it can be performed at different pH and temperature values for the additional characterisation and specification of enzymes. Enzyme activity is calculated from the increase in absorbance at 540 nm per unit time.

One unit of arabinase activity Is defined as the amount of enzyme (normalised for total assay volume) that gives an increase in $\Delta OD_{540\ nm}.min^{-1}$ under the conditions of the assay (pH 3.5 and 50° C.).

In some aspects, the enzyme composition according to the invention has beta-D-glucoside glucohydrolase activity or comprises a further enzyme having beta-D-glucoside glucohydrolase activity. Beta-D-glucoside glucohydrolase refers to enzymes of E.C 3.2.1.21.

In some aspects, the enzyme composition according to the invention has β-Xylosidase activity or comprises a further enzyme having β-Xylosidase activity. "β-Xylosidase" or "Xylan 1,4-beta-xylosidase" refers to enzymes of E.C 3.2.1.37. β-Xylosidase catalyze the hydrolysis of (1->4)-beta-D-xylans, to remove successive D-xylose residues from the non-reducing termini.

In some aspects of the invention, the enzyme composition according to the invention has cellobiohydrolase activity or comprises a further enzyme having cellobiohydrolase activity. "Cellobiohydrolase" or "Cellulose 1,4-beta-cellobiosidase" refers to enzymes of EC 3.2.1.91. Cellulose 1,4-beta-cellobiosidase catalyze hydrolysis of 1,4-beta-D-glucosidic linkages in cellulose and cellotetraose, releasing cellobiose from the non-reducing ends of the chains.

The cellobiohydrolase activity of the enzyme composition according to the invention is measured by the cellobiohydrolase assay as described in the following under the heading "Assays". The standard assay is carried out at pH 5.0, and it can be performed at different pH values for the additional characterisation and specification of enzymes.

One unit of cellobiohydrolase activity is defined as the amount of enzyme which produces 1 μmole p-nitrophenol from β-nitrophenyl 3-D-cellobiopyranoside per minute under the conditions of the assay (pH 5.0 (or as specified) and 50° C.).

In some aspects, the enzyme composition according to the invention has α-N-arabinofuranosidase activity or comprises a further enzyme having arabinofuranosidase activity. "α-N-arabinofuranosidase" or "Alpha-N-arabinofuranosidase" refers to enzymes of EC 3.2.1.55. α-N-arabinofuranosidase catalyze the hydrolysis of terminal non-reducing alpha-L-arabinofuranoside residues in alpha-L-arabinosides.

In one aspect of the invention, the arabinofuranosidase activity of the enzyme composition according to the invention is measured by the arabinofuranosidase assay as described in the following under the heading "Assays". The standard assay can be carried out at pH 5.0 and 50° C. and it can be performed at different values of pH and temperature for the additional characterisation and specification of enzymes.

One unit of α-N-arabinofuranosidase activity is defined as the amount of enzyme which produces 1 μmole p-nitrophenol from β-nitrophenyl α-L-arabinofuranoside per minute under the conditions of the assay (pH 5.0 and 50° C. (or as specified)).

In some aspects, the enzyme composition according to the invention has glucan 1,4-beta-glucosidase activity or comprises a further enzyme having glucan 1,4-beta-glucosidase activity. "Glucan 1,4-beta-glucosidase" or "glucan 1,4-beta-glucosidase" refers to enzymes of E.C3.2.1.74. Glucan 1,4-beta-glucosidase catalyze the hydrolysis of (1->4)-linkages in (1->4)-beta-D-glucans, to remove successive glucose units.

In some aspects, the enzyme composition according to the invention has xyloglucan-specific exo-beta-1,4-glucanase activity or comprises a further enzyme having xyloglucan-specific exo-beta-1,4-glucanase activity. "xyloglucan-specific exo-beta-1,4-glucanase" refers to enzymes of E.C3.2.1.155. Xyloglucan-specific exo-beta-1,4-glucanase catalyze the exohydrolysis of (1->4)-beta-D-glucosidic linkages in xyloglucan.

The enzymes and enzyme compositions according to the proceeding aspects may be used in a process comprising reducing the viscosity of an aqueous solution comprising a starch hydrolysate.

The enzymes and enzyme compositions may also be used in a process comprising filtering of an aqueous solution comprising a starch hydrolysate. In some embodiments the aqueous solution comprising a starch hydrolysate is a mash for beer making, and in other embodiments the aqueous solution comprising a starch hydrolysate is a food composition.

Alternatively, the enzyme composition according to the present invention may be used in the production of fruit juice, wine, grain processing, fuel alcohol, first—or second-generation biofuel, such as bioethanol, and potable alcohol.

In some embodiments the first—or second-generation biofuel, such as bioethanol is produced from agricultural feed stocks such as sugar cane, potato, corn, wheat sorghum etc. or from cellulosic material such as corn stover, switchgrass or other plant material. In both cases fermentable sugars are extracted from the raw material and fermented by microorganisms into alcohol, which is distilled and may be used as transportation fuel. The enzyme composition according to the present invention may be used in this production of biofuel. The enzymes complex may be added to enhance extraction of polysaccharides from the raw material, help degrade polysaccharides down into fermentable sugars and/or to enhance processing parameters such as separation of liquids from solids, flow characteristics and pumpability.

The process of the invention may be applied in the mashing of any grist. According to the invention the grist may comprise any starch and/or sugar containing plant material derivable from any plant and plant part, including tubers, roots, stems, leaves and seeds.

In some embodiments the grist comprises grain, such as grain from barley, wheat, rye, oat, corn, rice, milo, millet and sorghum, and more preferably, at least 10%, or more preferably at least 15%, even more preferably at least 25%, or most preferably at least 35%, such as at least 50%, at least 75%, at least 90% or even 100% (w/w) of the grist of the wort is derived from grain.

In some embodiments the grist comprises malted grain, such as barley malt. Preferably, at least 10%, or more preferably at least 15%, even more preferably at least 25%, or most preferably at least 35%, such as at least 50%, at least 75%, at least 90% or even 100% (w/w) of the grist of the wort is derived from malted grain.

The term "mash" is understood as aqueous starch slurry, e. g. comprising crushed barley malt, crushed barley, and/or other adjunct or a combination hereof, mixed with water later to be separated into wort+spent grains.

The term "mash separation" is understood as the separation of wort from spent grains, such as by lautering or mash filtration.

The term "beer filtration" is understood as a separation process in which the yeast cells and other turbidity-causing materials still present in the beer are removed, such as by microfiltration or membrane processes.

The enzyme preparation, such as in the form of a food ingredient prepared according to the present invention, may be in the form of a solution or as a solid—depending on the use and/or the mode of application and/or the mode of administration. The solid form can be either as a dried enzyme powder or as a granulated enzyme.

In one aspect the invention provides an enzyme composition preparation comprising the enzyme or enzyme composition according to the invention, an enzyme carrier and optionally a stabilizer and/or a preservative.

In yet a further aspect of the invention, the enzyme carrier is selected from the group consisting of glycerol or water.

In a further aspect, the preparation comprises a stabilizer. In one aspect, the stabilizer is selected from the group consisting of inorganic salts, polyols, sugars and combinations thereof. In one aspect, the stabilizer is an inorganic salt such as potassium chloride. In another aspect, the polyol is glycerol, propylene glycol, or sorbitol. In yet another aspect, the sugar is a small-molecule carbohydrate, in particular any of several sweet-tasting ones such as glucose, fructose and saccharose.

In yet at further aspect, the preparation comprises a preservative. In one aspect, the preservative is methyl paraben, propyl paraben, benzoate, sorbate or other food approved preservatives or a mixture thereof.

Specific Embodiments of the Invention

In some embodiments the enzyme exhibiting endo-1,4-β-xylanase activity, optionally in combination with any one or more β-glucanase according to the present invention provides for a significantly reduced viscosity in brewing applications facilitating improved mash and beer separation.

Desired xylanase characteristics for brewing applications may include one or more of the following aspects:
a) Enzyme substrate specificity
   WE-AX/WU-AX ratio has an impact on viscosity. In some embodiments this ratio is less than about 7.0, such as less than about 6.5, such as less than about 6.0, such as less than about 5.5, such as less than about 5.0, such as less than about 4.5.
b) Enzyme substrate selectivity
   How close to branch points the enzyme(s) cuts is believed to have an impact on the functionality.
c) Enzyme thermostability
   Continuous solubilisation of AX during mashing—thermostability a key feature. Accordingly, In some embodiments, the enzyme exhibiting endo-1,4-β-xylanase activity according to the present invention is thermostable within a temperature range of 65-78° C.
d) Enzyme pH optimum. Accordingly, in some embodiments, the enzyme exhibiting endo-1,4-β-xylanase activity has a pH optimum in the range of pH 5.4-5.6.
e) Enzyme inhibition (e.g. known key factor for xylanases)

Said significantly reduced viscosity in brewing applications may be measured as a reduced viscosity in the brewing application as compared to a control with a known enzyme or combination of enzyme activities, such as Ultraflo® Max used under same conditions and amounts.

In some embodiments, the enzyme exhibiting endo-1,4-β-xylanase activity according to the present invention, optionally in combination with any one or more β-glucanase according to the present invention provides for an improved mash and beer separation in brewing applications.

In some embodiments, the enzyme exhibiting endo-1,4-β-xylanase activity according to the present invention, optionally in combination with any one or more β-glucanase according to the present invention provides for a low potential for off flavour formation, such as off flavour formation related to arabinoxylan breakdown.

In some embodiments, the enzyme exhibiting endo-1,4-β-xylanase activity according to the present invention, optionally in combination with any one or more β-glucanase according to the present invention provides for a decreased risk of filter bed collapse, such as at lautering.

In some embodiments, the enzyme exhibiting endo-1,4-β-xylanase activity according to the present invention, optionally in combination with any one or more β-glucanase according to the present invention provides for a reduction in off flavour potential and/or reduction in off flavor formation. One aspect of the invention relates to an enzyme exhibiting endo-1,4-β-xylanase activity, which enzyme comprises an amino acid sequence having at least 80% identity with any one selected from SEQ ID NO:1, SEQ ID NO:2, SEQ ID NO:3, SEQ ID NO:4, SEQ ID NO:5, SEQ ID NO:6, SEQ ID NO:17, and SEQ ID NO:18, or any functional fragment thereof.

Another aspect relates to an enzyme exhibiting endo-1,3 (4)-β-glucanase activity, which enzyme comprises an amino acid sequence having at least 80% identity with any one selected from SEQ ID NO:7, SEQ ID NO:8, SEQ ID NO:9, SEQ ID NO:10, and SEQ ID NO:11, SEQ ID NO:12, SEQ ID NO:13, SEQ ID NO:14, SEQ ID NO:15, SEQ ID NO:16, or any functional fragment thereof.

In some embodiments of the invention the enzyme exhibiting endo-1,4-β-xylanase activity has a ratio in activity on soluble arabinoxylan substrate (WE-AX) to insoluble arabinoxylan substrate (WU-AX) arabinoxylan substrate of less than about 7.0, such as less than about 6.5, such as less than about 6.0, such as less than about 5.5, such as less than about 5.0, such as less than about 4.5.

In some embodiments the enzyme according to the invention has a temperature optimum in the range of 40-70° C., In some embodiments the enzyme according to the invention consists of the amino acid sequence identified by any one of SEQ ID NO: 1-18, or any functional fragment thereof.

A further important aspect of the invention relates to a composition comprising an enzyme exhibiting endo-1,4-β-xylanase activity according to the invention in combination with any one or more β-glucanase. In some embodiments this one or more β-glucanase is according to the invention.

A further important aspect of the invention is a composition comprising an enzyme exhibiting endo-1,3(4)-β-glucanase activity according to the invention in combination with any one or more xylanase. In some embodiments this one or more xylanase is an enzyme exhibiting endo-1,4-β-xylanase activity according to the invention. In some embodiments this one or more xylanase is an enzyme according to SEQ ID NO:17 and/or SEQ ID NO:18, or any functional fragment thereof.

In some embodiments the combination of an enzyme exhibiting endo-1,4-β-xylanase activity with an enzyme exhibiting endo-1,3(4)-β-glucanase activity is according to the following table:

| 2$^{nd}$ enzyme (Glucanase) | 1$^{st}$ enzyme (Xylanase) | | | | | | | |
| --- | --- | --- | --- | --- | --- | --- | --- | --- |
| | SEQ ID NO: 1 | SEQ ID NO: 2 | SEQ ID NO: 3 | SEQ ID NO: 4 | SEQ ID NO: 5 | SEQ ID NO: 6 | SEQ ID NO: 17 | SEQ ID NO: 18 |
| SEQ ID NO: 7 | X | X | X | X | X | X | X | X |
| SEQ ID NO: 8 | X | X | X | X | X | X | X | X |
| SEQ ID NO: 9 | X | X | X | X | X | X | X | X |
| SEQ ID NO: 10 | X | X | X | X | X | X | X | X |
| SEQ ID NO: 11 | X | X | X | X | X | X | X | X |
| SEQ ID NO: 12 | X | X | X | X | X | X | X | X |
| SEQ ID NO: 13 | X | X | X | X | X | X | X | X |
| SEQ ID NO: 14 | X | X | X | X | X | X | X | X |
| SEQ ID NO: 15 | X | X | X | X | X | X | X | X |
| SEQ ID NO: 16 | X | X | X | X | X | X | X | X | such as in the range of 45-65° C., such as in the range of 50-65° C., such as in the range of 55-65° C.

In some embodiments the enzyme according to the invention has at least 81, 82, 83, 84, 85, 86, 87, 88, 89, 90, 91, 92, 93, 94, 95, 96, 97, 98 or 99% identity with any one amino acid sequence selected from SEQ ID NO: 1-18, or any functional fragment thereof.

In some embodiments the enzyme according to the invention has a total number of amino acids of less than 350, such as less than 340, such as less than 330, such as less than 320, such as less than 310, such as less than 300 amino acids, such as in the range of 200 to 350, such as in the range of 220 to 345 amino acids.

In some embodiments the amino acid sequence of said enzyme according to the invention has at least one, two, three, four, five, six, seven, eight, nine or ten amino acid substitutions as compared to any one amino acid sequence selected from SEQ ID NO: 1-18, or any functional fragment thereof.

In some embodiments the amino acid sequence of said enzyme according to the invention has a maximum of one, two, three, four, five, six, seven, eight, nine or ten amino acid substitutions compared to any one amino acid sequence selected from SEQ ID NO: 1-18, or any functional fragment thereof.

In some embodiments the enzyme according to the invention comprises the amino acid sequence identified by any one of SEQ ID NO: 1-18, or any functional fragment thereof.

It is to be understood that any one of the above combination of a 1$^{st}$ enzyme being an enzyme exhibiting endo-1, 4-β-xylanase activity may be combined with one one enzyme exhibiting endo-1,3(4)-β-glucanase activity with a ratio between the two enzymes of 1:10, 2:10, 3:10, 4:10, 5:10, 6:10, 7:10, 8:10, 9:10, 10:10, 10:9, 10:8, 10:7, 10:6, 10:5, 10:4, 10:3, 10:2, or 10:1, such as within a range of 1:10-10:1, such as 2:10-10:2, such as 3:10-10:3, such as 4:10-10:4, such as 5:10-10:5, such as 6:10-10:6, such as 7:10-10:7, such as 8:10-10:8, or within 9:10-10:9.

In some embodiments the composition according to the invention comprises a combination of at least two enzymes, said two enzymes, or two enzymes with an amino acid sequence having at least 80% sequence identity with the respective SEQ ID, or any functional fragment thereof, being selected from the list consisting of SEQ ID NO:1 and SEQ ID NO:7;
SEQ ID NO:2 and SEQ ID NO:7;
SEQ ID NO:3 and SEQ ID NO:7;
SEQ ID NO:4 and SEQ ID NO:7;
SEQ ID NO:5 and SEQ ID NO:7;
SEQ ID NO:6 and SEQ ID NO:7;
SEQ ID NO:17 and SEQ ID NO:7;
SEQ ID NO:18 and SEQ ID NO:7;
SEQ ID NO:1 and SEQ ID NO:8;
SEQ ID NO:2 and SEQ ID NO:8;
SEQ ID NO:3 and SEQ ID NO:8;
SEQ ID NO:4 and SEQ ID NO:8;
SEQ ID NO:5 and SEQ ID NO:8;
SEQ ID NO:6 and SEQ ID NO:8;

SEQ ID NO:17 and SEQ ID NO:8;
SEQ ID NO:18 and SEQ ID NO:8;
SEQ ID NO:1 and SEQ ID NO:9;
SEQ ID NO:2 and SEQ ID NO:9;
SEQ ID NO:3 and SEQ ID NO:9;
SEQ ID NO:4 and SEQ ID NO:9;
SEQ ID NO:5 and SEQ ID NO:9;
SEQ ID NO:6 and SEQ ID NO:9;
SEQ ID NO:17 and SEQ ID NO:9;
SEQ ID NO:18 and SEQ ID NO:9;
SEQ ID NO:1 and SEQ ID NO:10;
SEQ ID NO:2 and SEQ ID NO:10;
SEQ ID NO:3 and SEQ ID NO:10;
SEQ ID NO:4 and SEQ ID NO:10;
SEQ ID NO:5 and SEQ ID NO:10;
SEQ ID NO:6 and SEQ ID NO:10;
SEQ ID NO:17 and SEQ ID NO:10;
SEQ ID NO:18 and SEQ ID NO:10;
SEQ ID NO:1 and SEQ ID NO:11;
SEQ ID NO:2 and SEQ ID NO:11;
SEQ ID NO:3 and SEQ ID NO:11;
SEQ ID NO:4 and SEQ ID NO:11;
SEQ ID NO:5 and SEQ ID NO:11;
SEQ ID NO:6 and SEQ ID NO:11;
SEQ ID NO:17 and SEQ ID NO:11;
SEQ ID NO:18 and SEQ ID NO:11;
SEQ ID NO:1 and SEQ ID NO:12;
SEQ ID NO:2 and SEQ ID NO:12;
SEQ ID NO:3 and SEQ ID NO:12;
SEQ ID NO:4 and SEQ ID NO:12;
SEQ ID NO:5 and SEQ ID NO:12;
SEQ ID NO:6 and SEQ ID NO:12;
SEQ ID NO:17 and SEQ ID NO:12;
SEQ ID NO:18 and SEQ ID NO:12;
SEQ ID NO:1 and SEQ ID NO:13;
SEQ ID NO:2 and SEQ ID NO:13;
SEQ ID NO:3 and SEQ ID NO:13;
SEQ ID NO:4 and SEQ ID. NO:13;
SEQ ID NO:5 and SEQ ID NO:13;
SEQ ID NO:6 and SEQ ID NO:13;
SEQ ID NO:17 and SEQ ID NO:13;
SEQ ID NO:18 and SEQ ID NO:13;
SEQ ID NO:1 and SEQ ID NO:14;
SEQ ID NO:2 and SEQ ID NO:14;
SEQ ID NO:3 and SEQ ID NO:14;
SEQ ID NO:4 and SEQ ID NO:14;
SEQ ID NO:5 and SEQ ID NO:14;
SEQ ID NO:6 and SEQ ID NO:14;
SEQ ID NO:17 and SEQ ID NO:14;
SEQ ID NO:18 and SEQ ID NO:14;
SEQ ID NO:1 and SEQ ID NO:15;
SEQ ID NO:2 and SEQ ID NO:15;
SEQ ID NO:3 and SEQ ID NO:15;
SEQ ID NO:4 and SEQ ID NO:15;
SEQ ID NO:5 and SEQ ID NO:15;
SEQ ID NO:6 and SEQ ID NO:15;
SEQ ID NO:17 and SEQ ID NO:15;
SEQ ID NO:18 and SEQ ID NO:15;
SEQ ID NO:1 and SEQ ID NO:16;
SEQ ID NO:2 and SEQ ID NO:16;
SEQ ID NO:3 and SEQ ID NO:16;
SEQ ID NO:4 and SEQ ID NO:16;
SEQ ID NO:5 and SEQ ID NO:16;
SEQ ID NO:6 and SEQ ID NO:16;
SEQ ID NO:17 and SEQ ID NO:16; and
SEQ ID NO:18 and SEQ ID NO:16.

In some embodiments the endo-1,3(4)-β-glucanase activity and the endo-1,4-β-xylanase activity are derived from at least two different enzymes, such as at least two different enzymes from two different species.

In some embodiments the total pressure built up is reduced to a value of less than 470 mm' WC, such as less than 450 mm WC, such as less than 430 mm WC, such as less than 410 mm WC, such as less than 390 mm WC, such as less than 370 mm WC, such as less than 350 mm WC, such as less than 330 mm WC, such as less than 310 mm WC, such as less than 300 mm WC, such as less than 290 mm WC, when the composition according to the present invention is used prior to the lautering in a brewing application.

In some embodiments the total pressure built up is reduced by at least 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 95% compared to the use of a negative control without said composition; when used prior to the lautering in a brewing application.

In some embodiments the wort filterability as measured by volume wort collected after 5 min of filtration relative to a control without enzymes is increased to above 1.5, such as above 1.6, such as above 1.7, such as above 1.8, such as above 1.9, such as above 2.0, such as above 2.1, such as above 2.2, such as above 2.3, such as above 2.4, such as, above 2.5, when the composition according to invention is used in a brewing application prior to the wort separation.

In some embodiments the wort filterability as measured by volume wort collected after 5 min of filtration is increased at least 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 110, 120, 130, 140, 150, 160, 170, 180, 190, 200, 210, 220, 230, 240, 250, 260, 270, 280, 290, or 300% as compared to the use of a negative control without said composition.

In some embodiments the composition according to the invention comprises any one or more further enzyme. In some embodiments the one or more further enzyme is selected from list consisting of a xylanase classified in EC 3.2.1.32, EC 3.2.1.136, or EC 3.2.1.156, a cellulase, a laminarinase, an endo-1,5-α-L-arabinanase, a beta-D-glucoside glucohydrolase, a β-Xylosidase, a celloblohydrolase, a glucan 1,4-beta-glucosidase, a xyloglucan-specific exo-beta-1,4-glucanase and an α-N-Arabinofuranosidase.

Sequences and enzymes identified by a sequence as mentioned herein and used according to the present invention alone or in combinations with other enzymes or compounds may be with or without signal peptide.

Assays

DNS Cellulase Activity Method (DNS CMC Method)

Systematic Name: 1,4-(1,3;1,4)-β-D-glucan 4-glucanohydrolase IUB Number: EC 3.2.1.4

Principle

The assay of cellulase is based on the enzymatic endo-hydrolysis of the 1,4-β-D-glucosidic bonds in carboxymethylcellulose (CMC), a α-1,4-glucan. The products of the reaction β-1,4 glucan oligosaccharides) was determined calorimetrically by measuring the resulting increase in reducing groups using a 3,5-dinitrosalicylic acid reagent. Enzyme activity was calculated from the relationship between the concentration of reducing groups, as glucose equivalents, and absorbance at 540 nm.

The assay was carried out at pH 5.0, but it can be performed at different pH values for the additional characterisation and specification of enzymes.

Unit Definition

One unit of cellulase activity is defined as the amount of enzyme which produces 1 µmole glucose equivalents per minute under the conditions of the assay (pH 5.0 (or as specified) and 50° C.).

Materials

Carboxymethylcellulose. Supplier: Megazyme Ltd. Product no.: CM-Cellulose 4M D-Glucose 'AnalaR'. Supplier: Merck Ltd (BDH). Product no.: 10117. M.W.: 180.16

Sodium acetate anhydrous 'AnalaR'. Supplier: Merck Ltd (BDH). Product no.: 10236. M.W.: 82.03

Acetic acid ("glacial") 'AnalaR'. Supplier: Merck Ltd (BDH). Product no.: 10001. M.W.: 60.05 3,5-Dinitrosalicylic acid GPR (3,5-dinitro-2-hydroxybenzoic acid). Supplier: Merck Ltd (BDH). Product no.: 28235

Sodium hydroxide pellets 'AnalaR'. Supplier: Merck Ltd (BDH). Product no.: 10252. M.W.: 40.00

Potassium sodium (+)-tartrate 'AnalaR'. Supplier: Merck Ltd (BDH). Product no.: 10219. M. W.: 282.22

1.5%(w/v solution) Carboxymethylcellulose (CMC) solution in 0.1M sodium acetate buffer, pH 5.0 (substrate solution).

3,5-Dinitrosalicylic acid (DNS) solution. 20 g/L of DNS in buffer containing 32 g/L sodium hydroxide pellets, and 600 g/L potassium sodium (+)-tartrate. Glucose standard solution (0.50 mg/ml)

Procedure

The enzyme composition was diluted into samples and a glucose standard curve as shown in FIG. 2 was made using glucose concentrations of 0, 0.125, 0.25, 0.375, and 0.5 mg/ml.

0.25 ml of enzyme solution was mixed with 1.75 ml of the substrate solution (1.5% w/v) at 50° C. and the reaction was stopped after 10 min by addition of DNS solution. This is followed by heating to 95° C. for 5 minutes.

The optical density was measured at 540 nm ($OD_{540nm}$) of the different samples.

Calculation

The enzyme activity is determined from the standard curve as shown in FIG. 2.

The activity is calculated as follows:

$$\text{Activity (u·ml}^{-1}\text{ or u·g}^{-1}) = \frac{T-c}{m} \times A \times \frac{1}{180 \cdot 16} \times 10^3 \times \frac{1}{V} \times \frac{1}{t} \times D$$

where:

$T = \Delta OD_{540\ nm}\text{TEST}$ $= OD_{540\ nm}\text{TEST} - OD_{540\ nm}\text{BLANK}$ $m$ = gradient of the standard curve (approximately 1.0)

$c$ = y axis intercept of the standard curve (always negative and approximately −0.02)

$180.16 \equiv$ molecular weight of glucose $10^3 \equiv$ to convert to µmoles $A \equiv$ assay volume in ml $V \equiv$ enzyme volume in ml $t \equiv$ assay time in minutes $D$ = actual enzyme dilution factor (e.g. for 1.000 g diluted to 1 liter $D = 1000$)

Laminarinase (DNS Laminarin Method)

Principle

The reaction, catalysed by laminarinase, involves the endohydrolysis of 1,3-glucosidic bonds in 1,3-β-D-glucans. Substrates include laminarin, paramylon and pachyman. The products of the reaction (β-1,3-glucan oligosaccharides) are determined colourimetrically by measuring the resulting increase in reducing groups using a 3,5-dintrosalicylic acid reagent. Enzyme activity is calculated from the relationship between the concentration of reducing groups, as glucose equivalents, and absorbance at 540 nm.

The assay was carried out at pH 5.0 and 50° C., but it can be performed at different values of pH and temperature for the additional characterisation and specification of enzymes.

Unit Definition

One unit of laminarinase activity is defined as the amount of enzyme which produces 1 µmole glucose equivalents per minute under the conditions of the assay (pH 5.0 and 50° C. (or as specified)).

Materials

See materials given above for the Cellulase activity assay.

Laminarin (from *Laminaria digitata*). Supplier: Sigma-Aldrich Co. Ltd. Product no.: L 9634

1.00%(w/v solution) Laminarin solution (substrate solution 0.1M sodium acetate buffer, pH 5.0)

1.75 ml laminarin solution is mixed with 0.25 ml diluted enzyme solution at 50° C. for 10 minutes and the reaction stopped by addition of 2 ml DNS solution.

Standard curve was made using 0, 0.125, 0.25, 0.5 and 0.75 mg/ml glucose solution.

Optical density was measured at 540 nm ($OD_{540\ nm}$).

Calculation

The activity is calculated as follows:

$$\text{Activity (u·ml}^{-1}\text{ or u·g}^{-1}) = \frac{T-c}{m} \times A \times \frac{1}{180 \cdot 16} \times 10^3 \times \frac{1}{V} \times \frac{1}{t} \times D$$

where:

$T = \Delta OD_{540\ nm}\text{TEST}$ $= OD_{540\ nm}\text{TEST} - OD_{540\ nm}\text{BLANK}$ $m$ = gradient of the standard curve (approximately 1.0)

$c$ = y axis intercept of the standard curve (always negative and approximately −0.03)

$180.16 \equiv$ molecular weight of glucose $10^3 \equiv$ to convert to µmoles $A \equiv$ assay volume in ml $V \equiv$ enzyme volume in ml $t \equiv$ assay time in minutes $D$ = enzyme dilution factor (e.g. for 1 g diluted to 1 liter $D = 1000$)

Arabinase Assay.

Principle

The assay of Arabinase activity is based on colorimetrically determination by measuring the resulting increase in reducing groups using a 3,5-dinitrosalicylic acid reagent. Enzyme activity was calculated from the relationship between the concentration of reducing groups, as arabinose equivalents, and absorbance at 540 nm.

The assay was carried out at pH 3.5, but it can be performed at different pH values for the additional characterisation and specification of enzymes.

Unit Definition

One unit of arabinase (Arabinanase (endo-1,5-alpha-L-arabinanase)) activity is defined as the amount of enzyme which produces 1 µmole arabinose equivalents per minute under the conditions of the assay (pH 3.5 (or as specified) and 50° C.).

Materials

Megazyme Sugar Beet Arabinan
Arabinose Sigma A3131 M.W.: 150.1 Sodium acetate anhydrous 'AnalaR'. Supplier: Merck Ltd (BDH). Product no.: 10236. M.W.: 82.03
Acetic acid ("glacial") 'AnalaR'. Supplier: Merck Ltd (BDH). Product no.: 10001. M.W.: 60.05 3,5-Dinitrosalicylic acid GPR (3,5-dinitro-2-hydroxybenzoic acid). Supplier: Merck Ltd (BDH). Product no.: 28235
Sodium hydroxide pellets 'AnalaR'. Supplier: Merck Ltd (BDH). Product no.: 10252. M.W.: 20-40.00
Potassium sodium (+)-tartrate 'AnalaR'. Supplier: Merck Ltd (BDH). Product no.: 10219. M.W.: 282.22
1.5%(w/v solution) Arabinan solution in 0.1M sodium acetate buffer, pH 3.5 (substrate solution).
3,5-Dinitrosalicylic acid (DNS) solution. 20 g/L of DNS in buffer containing 32 g/L sodium hydroxide pellets, and 600 g/L potassium sodium (+)-tartrate.
Arabinase standard solution (0.50 mg/ml)

Procedure

The enzyme composition was diluted into samples and a glucose standard curve was made using arabinase concentrations of 0, 0.125, 0.25, 0.375, and 0.5 mg/ml.

0.25 ml of enzyme solution was mixed with 1.75 ml of the substrate solution (1.5% w/v) at 50° C. and the reaction was stopped after 10 min by addition of DNS solution. Followed by heating to 95° C. for 5 minutes.

The optical density was measured at 540 nm ($OD_{540nm}$) of the different samples.

Calculation

The enzyme activity is determined from the standard curve.

The activity is calculated as follows:

$$\text{Activity (u·ml}^{-1}\text{ or u·g}^{-1}) = \frac{T-c}{m} \times A \times \frac{1}{150 \cdot 13} \times 10^3 \times \frac{1}{V} \times \frac{1}{t} \times D$$

where:

$$T = \Delta OD_{540\,nm}\text{TEST}$$
$$= OD_{540\,nm}\text{TEST} - OD_{540\,nm}\text{BLANK}$$

$m$ = gradient of the standard curve (approximately 1.0)

$c$ = $y$ axis intercept of the standard curve (always negative and approximately −0.02)

150.13 ≡ molecular weight of arabinase $10^3$ ≡ to convert to µmoles $A$ ≡ assay volume in ml $V$ ≡ enzyme volume in ml $t$ ≡ assay time in minutes $D$ = actual enzyme dilution factor (e.g. for 1.000 g diluted to 1 liter $D$ = 1000)

Arabinofuranosidase Assay.

The reaction, catalysed by α-N-arabinofuranosidase, involves the hydrolysis of the terminal bond, at the non-reducing α-L-arabinofuranoside residue, of α-L-arabinosides. The enzyme acts on α-L-arabinofuranosides, α-L-arabinans containing (1,3)- and/or (1,5)-linkages, arabinoxylans and arabinogalactans.

The assay of α-N-arabinofuranosidase is based upon the enzymatic hydrolysis of β-nitrophenyl α-L-arabinofuranoside. The assay is a "two-point", rather than a "continuous monitoring", method. The calculation of enzyme activity is based on measurements taken only at the beginning and end of the incubation period. A product of the reaction, β-nitrophenol is determined colourimetrically (after pH adjustment). Enzyme activity is calculated from the relationship between the concentration of p-nitrophenol and absorbance at 400 nm.

Preparation of Diluted Enzyme Solution:

Prepare all enzyme solutions, from powder or liquid enzyme preparations, with glass distilled water. Minimise assay dilution errors by avoiding large dilution steps involving small volumes or weights. In making enzyme dilutions it is more accurate, even for a liquid sample, to weigh out the initial enzyme sample. If this is done, in the case of liquid samples it is therefore necessary to measure the specific gravity of the liquid at 20° C.

As the assay is a "two-point", rather than a "continuous monitoring", method it is important to ensure the linearity within the incubation period with different enzyme systems and conditions. Under the standard assay conditions of substrate concentration, pH, temperature and assay time the assay has been demonstrated to be linear in the range $\Delta OD_{540nm}$ TEST (T)=0.20-1.50. However, for good practice, the assay is operated within a defined range of $\Delta OD_{540nm}$ TEST (T)=0.400-0.800.

Procedure

Each enzyme sample assay involves three analyses: duplicate test (TEST) analyses and a blank (BLANK) analysis. The procedure given describes the analysis of a single enzyme sample.

|  | TEST | BLANK |
| --- | --- | --- |
| 0.2M Sodium acetate buffer, pH 5.0 | 1.00 ml | 1.00 ml |
| Glass distilled water | 1.00 ml | 1.00 ml |
| p-Nitrophenyl-α-L-arabinofuranoside solution | 1.00 ml | 1.00 ml |

0.25 ml diluted enzyme solution was added to the solutions at 50° C., the reaction was stopped after 10 minutes by addition of 4 ml of 0.4M glycine solution, pH 10.8 (stop reagent).

Absorbance was measured at 400 nm at 25° C. against a water blank.

determine $OD_{400nm}$ TEST for the duplicate TESTS measured;

determine $OD_{400nm}$ BLANK.

Calculation $$\Delta OD_{400\,nm}\text{TEST}(T) = OD_{400\,nm}\text{TEST} - OD_{400\,nm}\text{BLANK}$$

$$\text{Units}(\mu\text{mol·min}^{-1}) = \frac{T}{18300} \times \frac{V}{1000} \times 10^6 \times \frac{1}{t}$$

$$\text{Activity (u·ml}^{-1}\text{ or u·g}^{-1}) = \text{Units} \times \frac{1}{E} \times D$$

where: T=OD400 nm TEST−OD400 nm BLANK
18300=Molar extinction coefficient for p-nitrophenol (1 cm path length)
V=7.25 (total liquid volume in test in nil)

t=10 (minutes)
1 u=1 µmol·min-1
E=0.25 (volume of diluted enzyme sample in ml)
D=Enzyme dilution factor e.g. for 1 ml diluted to 1 liter D=1000)

Cellobiohydrolase Assay.

Principle

The reaction, catalysed by cellobiohydrolase, involves the hydrolysis of 1,4-β-D-glucosidic linkages in cellulose and cellotetraose, releasing cellobiose from the non-reducing ends of the chains.

The assay of cellobiohydrolase is based on the enzymatic hydrolysis of p-nitrophenyl β-D-cellobiopyranoside. The product of the reaction, p-nitrophenol is determined colorimetrically (after pH adjustment). Enzyme activity is calculated from the relationship between the concentration of p-nitrophenol and absorbance at 400 nm.

The assay is operated within the linear defined range of $\Delta OD_{540nm}$ TEST (T)=0.400-0.800.

Procedure

Each enzyme sample assay involves three analyses: duplicate test (TEST) analyses and a blank (BLANK) analysis. The procedure given describes the analysis of a single enzyme sample.

|  | TEST | BLANK |
| --- | --- | --- |
| 0.2M Sodium acetate buffer, pH 5.0 | 1.00 ml | 1.00 ml |
| Glass distilled water | 1.00 ml | 1.00 ml |
| p-Nitropheny β-D-cellobiopyranoside solution | 1.00 ml | 1.00 ml |

0.25 ml diluted enzyme solution was added to the test solution at 50° C., after 30 minutes 4 ml of 0.4M glycine solution, pH 10.8 (stop reagent) was added to each tube.

Absorbance was measured at 20° C. at 400 nm in a 1 cm glass cuvette against a water blank.
determine OD400 nm TEST for the duplicate TESTS measured;
determine OD400 nm BLANK.

Calculation $$\Delta OD_{400\,nm}\text{TEST}(T) = OD_{400\,nm}\text{TEST} - OD_{400\,nm}\text{BLANK}$$

$$\text{Units}(\mu mol \cdot min^{-1}) = \frac{T}{18300} \times \frac{V}{1000} \times 10^6 \times \frac{1}{t}$$

$$\text{Activity } (u \cdot ml^{-1} \text{ or } u \cdot g^{-1}) = \text{Units} \times \frac{1}{E} \times D$$

where: T=$OD_{400nm}$ TEST−$OD_{400nm}$ BLANK
18300=Molar extinction coefficient for p-nitrophenol (1 cm path length)
v=7.25 (total liquid volume in test in ml)
1000=to convert to liters
$10^6$=to convert to µmoles
t=30 (minutes)
1 u=1 µmol·min$^{-1}$
E=0.25 (volume of diluted enzyme sample in ml)
D=Enzyme dilution factor e.g. for 1 ml diluted to 1 liter D=1000)

Numbered Embodiments According to the Invention

1. An enzyme exhibiting endo-1,4-β-xylanase activity, which enzyme comprises an amino acid sequence having at least 80% identity with any one selected from SEQ ID NO:1, SEQ ID NO:2, SEQ ID NO:3, SEQ ID NO:4, SEQ ID NO:5, SEQ ID NO:6, SEQ ID NO:17, and SEQ ID NO:18, or any functional fragment thereof.

2. The enzyme according to embodiment 1, which enzyme has a ratio in activity on soluble arabinoxylan substrate (WE-AX) to insoluble arabinoxylan substrate (WU-AX) arabinoxylan substrate of less than about 7.0, such as less than about 6.5, such as less than about 6.0, such as less than about 5.5, such as less than about 5.0, such as less than about 4.5.

3. An enzyme exhibiting endo-1,3(4)-β-glucanase activity, which enzyme comprises an amino acid sequence having at least 80% identity with any one selected from SEQ ID NO:7, SEQ ID NO:8, SEQ ID NO:9, SEQ ID NO:10, and SEQ ID NO:11, SEQ ID NO:12, SEQ ID NO:13, SEQ. ID NO:14, SEQ ID NO:15, SEQ ID NO:16, or any functional fragment thereof.

4. The enzyme according to any one of embodiment 1-3, which enzyme has a temperature optimum in the range of 40-70° C., such as in the range of 45-65° C., such as in the range of 50-65° C., such as in the range of 55-65° C.

5. The enzyme according to any one of embodiments 1-4, wherein said enzyme has at least 81, 82, 83, 84, 85, 86, 87, 88, 89, 90, 91, 92, 93, 94, 95, 96, 97, 98 or 99% identity with any one amino acid sequence selected from SEQ ID NO: 1-18, or any functional fragment thereof.

6. The enzyme according to any one of embodiments 1-5 having a total number of amino acids of less than 350, such as less than 340, such as less than 330, such as less than 320, such as less than 310, such as less than 300 amino acids, such as in the range of 200 to 350, such as in the range of 220 to 345 amino acids.

7. The enzyme according to any one of embodiments 1-6, wherein the amino acid sequence of said enzyme has at least one, two, three, four, five, six, seven, eight, nine or ten amino acid substitutions as compared to any one amino acid sequence selected from SEQ ID NO: 1-18, or any functional fragment thereof.

8. The enzyme according to any one of embodiments 1-7, wherein the amino acid sequence of said enzyme has a maximum of one, two, three, four, five, six, seven, eight, nine or ten amino acid substitutions compared to any one amino acid sequence selected from SEQ ID NO: 1-18, or any functional fragment thereof.

9. The enzyme according to any one of embodiments 1-8, which enzyme comprises the amino acid sequence identified by any one of SEQ ID NO: 1-18, or any functional fragment thereof.

10. The enzyme according to any one of embodiments 1 or 3, which enzyme consists of the amino acid sequence identified by any one of SEQ ID NO: 1-18, or any functional fragment thereof.

11. A DNA construct comprising a DNA sequence encoding an enzyme according to any of embodiments 1-10.

12. A recombinant expression vector comprising a DNA construct according to embodiment 11.

13. A cell that has been transformed with a DNA construct of embodiment 11 or the vector of embodiment 12.

14. A preparation comprising an enzyme according to any one of embodiments 1-10, or a DNA construct according to embodiment 11, or a vector according to embodiment 12, or a cell according to embodiment 13.

15. A composition comprising an enzyme exhibiting endo-1,4-β-xylanase activity according to any one of embodiments 1, 2, 4-10 in combination with any one or more β-glucanase.

16. The composition according to embodiment 15, wherein said one or more β-glucanase is an enzyme exhibiting endo-1,3(4)-β-glucanase activity according to any one of embodiments 3-10.
17. A composition comprising an enzyme exhibiting endo-1,3(4)-β-glucanase activity according to any one of embodiments 3-10 in combination with any one or more xylanase.
18. The composition according to embodiment 17, wherein said one or more xylanase is an enzyme exhibiting endo-1,4-β-xylanase activity according to any one of embodiments 1, 2, 4-10.
19. The composition according to any one of embodiments 15-18, wherein said endo-1,3(4)-β-glucanase activity and said endo-1,4-β-xylanase activity are derived from at least two different enzymes, such as at least two different enzymes from two different species.
20. The composition according to any one of embodiments 15-19, comprising a combination of at least two enzymes, said two enzymes, or two enzymes with an amino acid sequence having at least 80% sequence identity with the respective SEQ ID, or any functional fragment thereof, being selected from the list consisting of SEQ ID NO:1 and SEQ ID NO:7;
SEQ ID NO:2 and SEQ ID NO:7;
SEQ ID NO:3 and SEQ ID NO:7;
SEQ ID NO:4 and SEQ ID NO:7;
SEQ ID NO:5 and SEQ ID NO:7;
SEQ ID NO:6 and SEQ ID NO:7;
SEQ ID NO:17 and SEQ ID NO:7;
SEQ ID NO:18 and SEQ ID NO:7;
SEQ ID NO:1 and SEQ ID NO:8;
SEQ ID NO:2 and SEQ ID NO:8;
SEQ ID NO:3 and SEQ ID NO:8;
SEQ ID NO:4 and SEQ ID NO:8;
SEQ ID NO:5 and SEQ ID NO:8;
SEQ ID NO:6 and SEQ ID NO:8;
SEQ ID NO:17 and SEQ ID NO:8;
SEQ ID NO:18 and SEQ ID NO:8;
SEQ ID NO:1 and SEQ ID NO:9;
SEQ ID NO:2 and SEQ ID NO:9;
SEQ ID NO:3 and SEQ ID NO:9;
SEQ ID NO:4 and SEQ ID NO:9;
SEQ ID NO:5 and SEQ ID NO:9;
SEQ ID NO:6 and SEQ ID NO:9;
SEQ ID NO:17 and SEQ ID NO:9;
SEQ ID NO:18 and SEQ ID NO:9;
SEQ ID NO:1 and SEQ ID NO:10;
SEQ ID NO:2 and SEQ ID NO:10;
SEQ ID NO:3 and SEQ ID NO:10;
SEQ ID NO:4 and SEQ ID NO:10;
SEQ ID NO:5 and SEQ ID NO:10;
SEQ ID NO:6 and SEQ ID NO:10;
SEQ ID NO:17 and SEQ ID NO:10;
SEQ ID NO:18 and SEQ ID NO:10;
SEQ ID NO:1 and SEQ ID NO:11;
SEQ ID NO:2 and SEQ ID NO:11;
SEQ ID NO:3 and SEQ ID NO:11;
SEQ ID NO:4 and SEQ ID NO:11;
SEQ ID NO:5 and SEQ ID NO:11;
SEQ ID NO:6 and SEQ ID NO:11;
SEQ ID NO:17 and SEQ ID NO:11;
SEQ ID NO:18 and SEQ ID NO:11;
SEQ ID NO:1 and SEQ ID NO:12;
SEQ ID NO:2 and SEQ ID NO:12;
SEQ ID NO:3 and SEQ ID NO:12;
SEQ ID NO:4 and SEQ ID NO:12;
SEQ ID NO:5 and SEQ ID NO:12;
SEQ ID NO:6 and SEQ ID NO:12;
SEQ ID NO:17 and SEQ ID NO:12;
SEQ ID NO:18 and SEQ ID NO:12;
SEQ ID NO:1 and SEQ ID NO:13;
SEQ ID NO:2 and SEQ ID NO:13;
SEQ ID NO:3 and SEQ ID NO:13;
SEQ ID NO:4 and SEQ ID NO:13;
SEQ ID NO:5 and SEQ ID NO:13;
SEQ ID NO:6 and SEQ ID NO:13;
SEQ ID NO:17 and SEQ ID NO:13;
SEQ ID NO:18 and SEQ ID NO:13;
SEQ ID NO:1 and SEQ ID NO:14;
SEQ ID NO:2 and SEQ ID NO:14;
SEQ ID NO:3 and SEQ ID NO:14;
SEQ ID NO:4 and SEQ ID NO:14;
SEQ ID NO:5 and SEQ ID NO:14;
SEQ ID NO:6 and SEQ ID NO:14;
SEQ ID NO:17 and SEQ ID NO:14;
SEQ ID NO:18 and SEQ ID NO:14;
SEQ ID NO:1 and SEQ ID NO:15;
SEQ ID NO:2 and SEQ ID NO:15;
SEQ ID NO:3 and SEQ ID NO:15;
SEQ ID NO:4 and SEQ ID NO:15;
SEQ ID NO:5 and SEQ ID NO:15;
SEQ ID NO:6 and SEQ ID NO:15;
SEQ ID NO:17 and SEQ ID NO:15;
SEQ ID NO:18 and SEQ ID NO:15;
SEQ ID NO:1 and SEQ ID NO:16;
SEQ ID NO:2 and SEQ ID NO:16;
SEQ ID NO:3 and SEQ ID NO:16;
SEQ ID NO:4 and SEQ ID NO:16;
SEQ ID NO:5 and SEQ ID NO:16;
SEQ ID NO:6 and SEQ ID NO:16;
SEQ ID NO:17 and SEQ ID NO:16; and
SEQ ID NO:18 and SEQ ID NO:16.

21. The composition according to any one of embodiments 15-20, wherein when used prior to the lautering in a brewing application the total pressure built up is reduced to a value of less than 470 mm WC, such as less than 450 mm WC, such as less than 430 mm WC, such as less than 410 mm WC, such as less than 390 mm WC, such as less than 370 mm WC, such as less than 350 mm WC, such as less than 330 mm WC, such as less than 310 mm WC, such as less than 300 mm WC, such as less than 290 mm WC.
22. The composition according to any one of embodiments 15-21, wherein when used prior to the lautering in a brewing application the total pressure built up is reduced by at least 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 95% compared to the use of a negative control without said composition.
23. The composition according to any one of embodiments 15-22; wherein when used in a brewing application prior to the wort separation, the wort filterability as measured by volume wort collected after 5 min of filtration relative to a control without enzymes is increased to above 1.5, such as above 1.6, such as above 1.7, such as above 1.8, such as above 1.9, such as above 2.0, such as above 2.1, such as above 2.2, such as above 2.3, such as above 2.4, such as above 2.5.
24. The composition according to any one of embodiments 15-23, when used in a brewing application prior to the wort separation, the wort filterability as measured by volume wort collected after 5 min of filtration is increased by at least 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 110, 120, 130, 140, 150, 160, 170, 180, 190, 200, 210, 220, 230, 240, 250, 260, 270, 280, 290, or 300% as compared to the use of a negative control without said composition.

25. The composition according to any one of embodiments 15-24, comprising any one or more further enzyme.
26. The composition according to embodiment 25, wherein said one or more further enzyme is selected from list consisting of a xylanase classified in EC 3.2.1.32, EC 3.2.1.136, or EC 3.2.1.156, a cellulase, a laminarinase, an endo-1,5-α-L-arabinanase, a beta-D-glucoside glucohydrolase, a β-Xylosidase, a cellobiohydrolase, a glucan 1,4-beta-glucosidase, a xyloglucan-specific exo-beta-1,4-glucanase and an α-N-Arabinofuranosidase.
27. Use of an enzyme according to embodiments 1-10, or a preparation according to embodiment 14, or a composition according to any one of embodiments 15-26 in the production of a food, feed, or malt beverage product.
28. Use of an enzyme according to, embodiments 1-10, or a preparation according to embodiment 14, or a composition according to any one of embodiments 15-26, in the production of dough or baked products.
29. Use of an enzyme according to embodiments 1-10, or a preparation according to embodiment 14, or a composition according to any one of embodiments 15-26, in the preparation of pulp or paper.
30. Use of an enzyme according to embodiments 1-10, or a preparation according to embodiment 14, or a composition according to any one of embodiments 15-26, for the preparation of cereal components.
31. The use according to embodiment 29, in which the cereal is rye, wheat, or barley.
32. Use of enzyme according to embodiments 1-10, or a preparation according to embodiment 14, or a composition according to any one of embodiments 15-26, In the production of beer or modification of by-products from a brewing process.
33. Use of enzyme according to embodiments 1-10, or a preparation according to embodiment 14, or a composition according to any one of embodiments 15-26, in the production of wine or juice.
34. Use of enzyme according to embodiments 1-10, or a preparation according to embodiment 14, or a composition according to any one of embodiments 15-26, in the production of a first—or second-generation biofuel, such as bioethanol.
35. Method of altering filterability of a starch comprising material, said method comprising the step of treating said starch comprising material with enzyme according to embodiments 1-10, or a preparation according to embodiment 14, or a composition according to any one of embodiments 15-26.
36. Method of reducing pressure built up during lautering in a brewing application, said method comprising the step of treating a brewing mash with enzyme according to embodiments 1-10, or a preparation according to embodiment 14, or a composition according to any one of embodiments 15-26.
37. Method for the production of a food, feed, or beverage product, such as an alcoholic or non-alcoholic beverage, such as a cereal- or malt-based beverage like beer or whiskey, said method comprising the step of treating a starch comprising material with enzyme according to embodiments 1-10, or a preparation according to embodiment 14, or a composition according to any one of embodiments 15-26.
38. Method for the production of a brewing mash, said method comprising the step of treating a starch comprising material with enzyme according to embodiments 1-10, or a preparation according to embodiment 14, or a composition according to any one of embodiments 15-26.
39. Method for the production of a first—or second-generation biofuel; such as bioethanol, said method comprising the step of treating a starch comprising material with an enzyme according to embodiments 1-10, or a preparation according to embodiment 14, or a composition according to any one of embodiments 15-26.
40. Product obtained by the method according to any one of embodiments 38-39.
41. A composition comprising the product according to embodiment 40, such as wherein the product is in a range of 0.1%-99.9%.

EXAMPLES

Example 1

Methods and results in relation to xylanases/glucanase filing for brew application. The below methods have been used to screen for xylanases and glucanases with application in brewing:

Methods:

Water Extractable Arabinoxvlan (WE-AX) Xylanase Method:

Samples, to obtain approx. OD540=0.25-0.30 in this assay and xylose standards (0, 0.125, 0.250, 0.375 and 0.500 mg/ml distilled water) are prepared in distilled water. At time t=0 minutes, 1.75 ml soluble wheat arabinoxylan (0.5% wheat arabinoxylan (PWAXYH, Megazyme, Bray, Ireland)) in 0.1M sodium acetate/acetic acid, pH 5) is placed in a test tube at 50° C. At time t=5 minutes, 250-enzyme solution is added to the substrate at 50° C. followed by mixing. Distilled water is used as blank. At time t=15 minutes, 2 ml DNS solution. (1% 3,5-Dinitrosalicylic acid (DNS), 1.6% sodium hydroxide, 30% potassium sodium tartrate in distilled water) is added to the enzyme-substrate solution and 2.0 ml standard solution. Samples, blanks and standards added DNS are placed in a boiling water bath (95° C.) for 5 minutes. Hereafter samples, blanks and standards are cooled by placing them in a 25° C. water bath for 20 minutes. The Optical density of all samples are read at OD540 using a spectrophotometer. Based on the dilution of the samples, the amount of sample taking into work and the standards, the xylanases activity of the sample can be calculated.

One Unit of endo-1,4-beta-xylanase WE-AX activity is defined as the amount of enzyme which produces 1 μmole xylose equivalents per minute under the conditions mentioned above (Water extractable arabinoxylan (WE-AX) xylanase method).

Water Un-Extractable Arabinoxvlan (WU-AX) Xylanase Method:

Samples are prepared in distilled water. At time t=0 minutes, 1.75 ml Insoluble wheat (0.5% wheat arabinoxylan (PWAXYI, Megazyme, Bray, Ireland)) in 0.1M sodium acetate/acetic adic, pH 5) is placed in a test tube at 50° C. At time t=5 minutes, 250 μl enzyme solution is added to the substrate at 50° C. followed by mixing. Distilled water is used as blank. At time t=15 minutes, samples and blanks are placed in a boiling water bath (95° C.) for 5 minutes.

Hereafter samples and blanks are centrifuged to precipitate residual insoluble substrate. The amount of arabinoxylan brough into solution is determined using the method described by Rouau, X. and Surget, A. (1994), Carbohydrate Polymers, 24, 123-132.

WU-AX endo-1,4-beta-xylanase activity is defined as the amount of pentoses solubilised (μg pentoses) under the conditions described above giving a unit definition of μg pentose/gram of xylanase sample.

Xylanase Activity Assay

Samples, to obtain approx. OD540=0.25-0.30 in this assay and xylose standards (0, 0.125, 0.250, 0.375 and 0.500 mg/ml distilled water) are prepared in distilled water. At time t=0 minutes, 1.75 ml soluble wheat arabinoxylan (0.5% wheat arabinoxylan (PWAXYH, Megazyme, Bray, Ireland)) in 0.1M sodium acetate/acetic acid, pH 5) is placed in a test tube at 50° C. At time t=5 minutes, 250 μl enzyme solution is added to the substrate at 50° C. followed by mixing. Distilled water is used as blank. At time t=15 minutes, 2 ml DNS solution (1% 3,5-Dinitrosalicylic acid (DNS), 1.6% sodium hydroxide, 30% potassium sodium tartrate in distilled water) is added to the enzyme-substrate solution and 2.0 ml standard solution. Samples, blanks and standards added DNS are placed in a boiling water bath (95° C.) for 5 minutes. Hereafter samples, blanks and standards are cooled by placing them in a 25° C. water bath for 20 minutes. The Optical density of all samples are read at OD540 using a spectrophotometer. Based on the dilution of the samples, the amount of sample taking into work and the standards, the xylanases activity of the sample can be calculated.

One Unit of endo-1,4-beta-xylanase WE-AX activity is defined as the amount of enzyme which produces 1 μmole xylose equivalents per minute under the conditions mentioned above Glucanase Activity Assay Samples, to obtain $OD_{540}$ within the standard curve in this assay and glucose standards (0; 0.125; 0.250; 0.500; and 0.750 mg/ml distilled water) are prepared in distilled water. At time t=0 minutes, 1,75 ml barley beta-glucan (1.5% barley beta-glucan (P-BGBM, Megazyme, Bray, Ireland)) in 1M sodium acetate/acetic adic, pH 5) is placed in a test tube at 50° C. At time t=5 minutes, 250 μl enzyme solution is added to the substrate at 50° C. followed by mixing. Distilled water is used as blank. At time t=15 minutes, 2 ml DNS solution (1% 3,5-Dinitrosalicylic acid (DNS), 1,6% sodium hydroxide, 30% potassium sodium tartrate in distilled water) is added to the enzyme-substrate solution and 2.0 ml standard solution. Samples, blanks and standards added DNS are placed in a boiling water bath (95° C.) for 15 minutes. Hereafter samples, blanks and standards are cooled by placing them in a 25° C. water bath for 20 minutes. The Optical density of all samples are read at $OD_{540}$ using a spectrophotometer. Based on the dilution of the samples, the amount of sample taking into work and the standards, the glucanase activity of the sample can be calculated.

One unit of endo-1,3(4)-β-glucanase activity is defined as the amount of enzyme which produces 1 μmole glucose equivalents per minute under the conditions of the assay (pH 5.0 (or as specified) and 50° C.).

Lab Scale Brewing Application Method:

Lab scale brewing application studies were conducted using Pilsner malt: Barley in a 75:25 ratio at a water:grist ratio of 3:1 (150 ml:50 g grist). Initially water was preheated to 53° C. before mashing in and pH adjustment (5.4, 2 M H2SO4). After regaining initial temperature (10 min period) the mashing profile (see FIG. 1) is initiated and enzymes are added. After mashing off wort separation is conducted using a conventional plastic funnel and filter paper (paper filter No 1, 24 cm diameter, Whatman, England). Filtration performance was evaluated as well as several other wort parameters, such as i.e. viscosity, β-glucan and pentosan.

Wort filtration was measured for 30 min after which filtration was terminated. Collected wort was cooled before any further analysis.

Filtration

Filtration data are presented as volume wort collected after 5, 10, 15 and 30 minutes relative to a blank (brewing without added exogenous enzymes).

Pilot Scale Brewing

Trials were conducted in a pilot scale brewing facility (2 HL capacity). Wort separation was conducted by lautering and beer filtration by horizontal kiselguhr filtration.

To elucidate filtration optimization by combination of glucanase and xylanase under "challenging" brewing conditions, pilot scale brewing trails were conducted using a mixed grist comprising of 75% malt and 25% barley. Initially, the water:grist ratio was set at 2.8:1 (mash start) increasing to 3.1:1 at the start of lautering. In comparison water:grist ratios around 3.2-3.8 are typical in full scale brew house lautering. Thus the current pilot trial settings of a 3.1:1 water:grist ratio are believed to be in the challenging end of the scale.

Malt and barley was ground dry using a two-roller mill. Both barley and malt was milled twice using a roller distance of ~0.7 mm.

Mashing-in was conducted aiming at an initial mash temperature of 53° C. After mashing-in small adjustments were conducted such as: mash volume adjustment for water:grist ratio of 2.8:1 and pH adjustment to ~5.56 (Lactic acid). After fine tuning the mash, enzyme was added and the mashing profile given in FIG. 1 was followed. Saccharification rest at 70° C. was programmed to 15 min, however rest period was extended by 5 min until an Iodine test showed that no starch was present. (Ludwig Narziss and Werner Back, Technische Universitaet Muenchen (Fakultaet fuer Brauwesen, Weihenstephan), Abriss der Bierbrauerel. WILEY-VCH Verlags GmbH Weinheim Germany, 2005).

Mashing-off was initiated after a 5 min rest at 78° C. Mash was transferred to the Lauter Tun, which was beforehand prefilled with water to a height just below the "false bottom". The mash was left to rest for 5 min for settling of filter cake. This was followed by a 15 min recirculation (140 L/h) ensuring filter cake settling and wort clarification. Typically in full scale brewing, filtration will be initiated when a given wort turbidity is obtained, however in the current trials recirculation was kept constant at 15 min enabling comparison of trials. During lautering the following data were collected, including time (min), wort volume collected (L), filtration pressure difference across filter cake (mmWC, mm Water Column), pump capacity (%), wort turbidity (EBC) and mash temperature (° C.).

The pressure build up across the filter cake during filtration is believed to be a factor contributing to setting the standard of the wort lautering performance. Reaching very high pressure differences—e.g. 250 mmWC during first wort collection and e.g. 450 mmWC for the reminder of the lautering—a filter cake racking (also known as deep cut) is induced. Racking is a process where a filter cake collapses or a filtration channel formation is relieved by slowing cutting the filter cake with special designed knives. Following filter cake racking a 6 min wort recirculation (flow rate: 120 l/h) was introduced priming the filter cake for continued filtration. Filter cake racking relieves an otherwise compromised filtration performance which would otherwise also result in poor wort quality. If no pressure induced racking has been introduced by the beginning of the 3rd sparging, automatic rackings were conducted at the beginning of the 3rd and 4th spargings to ensure that no full filtration block would occur just before finishing wort separation.

Lautering was conducted with the settings illustrated in table 1.

TABLE 1

Lautering settings. Volumes collected (L), filtration flow (L/h) and Sparging volumes (L).

| Wort | Volume collected, L | Filtration flow, L/h | Sparging volume, L |
|---|---|---|---|
| First wort | 0-60 | 130 | |
| 1st sparging | 60-78 | 140 | 18 |
| 2nd sparging | 78-96 | 160 | 18 |
| 3rd sparging | 96-114 | 180 | 18 |
| 4th sparging | 114-140 | 180 | 26 |

After end lautering, sweet wort was returned to the Mash Tun, heated to boiling and hops were added. Hopping was continued for 80 min and at the end of hopping pH is adjusting to 5.10±0.05. Hops were cleared from the bitter wort by use of whirlpool and following wort was cooled to ~8° C. For fermentation, a bottom fermenting dried yeast (*Saccharomyces cerevisiae*) W34/70 from Fermentis was chosen. Yeast was rehydrated for 30 min and pitched at 100 g/HL. Main fermentation was hold for 5-6 days at 10° C., followed by maturation at 15° C. until attenuated and Diacetyl below 80 ppb. Beer was stored for another 2-3 weeks at 1° C. and 0.7 bar before filtering.

Beer was filtered horizontally by use of 1.2 μm PP-candle plates and kieselguhr. Up to 8 plates could be included in the filtration unit, resulting in a total filtration area of ~0.5 m2. In the current studies 3 plates were included and filtration was conducted at a flow rate of 130 L/h, resulting in a speed of filtration of 6.9 HL/(h·m2). In full scale breweries, speed of filtration is usually set between 5-7 HL/(h·m2). It is thus obvious that the current settings are in the high end—a deliberate choice challenging the beer filtration conditions to verify potential benefits from the choice of using an enzyme in the brewing process. During beer filtration, flow rates (L/h) as well as pressure values (P-in and P-out) were monitored to verify beer filtration performance. Also a number of beer analyses, such as Original Gravity (OG), Apparent Extract (AE), Alcohol By Volume (ABV), Apparent Degree of Fermentation (ADF), Reel Degree of Fermentation (RDF), pH, colour and bitterness were conducted for evaluation of beer quality.

Results:

Xylanases:

Xylanases were screened for their activity on soluble substrate and insoluble substrate, their pH and temperature characteristics.

Results are shown in table 2.

TABLE 2

Xylanases screened, their activity on soluble (WE-AX) and insoluble (WU-AX) arabinoxylan subtrate and their biochemical characteristics in regard to temp and pH.

| Name | Origin | GH | WE-AX | WU-AX | WU-AX/ WE-AX | Temp opt, ° C. | T½ temp, ° C. | pH opt. |
|---|---|---|---|---|---|---|---|---|
| AfuXyn2 | *Aspergillus fumingatus* | 11 | 7798 | 68790526 | 8822 | 65 | 59 | 5.5 |
| AfuXyn3 | *Aspergillus fumingatus* | 11 | 26283 | 99716865 | 3794 | 60 | 62 | 5 |
| AfuXyn5 | *Aspergillus fumingatus* | 11 | 90005 | 714363158 | 7937 | 60 | 50 | 4 |
| BsuXyn3 | *Bacillus subtilis*, BS3 | 11 | 82 | 1095357 | 13388 | 50 | n.d. | 6 |
| BsuXyn4 | *subtilis*, BS4 #160 | 11 | 54 | 1005400 | 18619 | 50 | n.d. | 6 |
| TerXyn1 | *Geosmithia emersonii* | 10 | 1467 | 6208786 | 4232 | 78 | >78 | 3 |
| AtuXyn3 | *Aspergillus tubigensis* | 10 | 1220 | 7760982 | 6361 | 65 | 67 | 4.5 |
| AtuXyn4 | *Aspergillus tubigensis* | 11 | 1600 | 12934971 | 8084 | 45 | 58 | 5 |
| AacXyn2 | *Aspergillus aculeatus* | 10 | 777 | 3880491 | 4994 | 70 | 73 | 4 |
| TreXyn2 | *Trichoderma reesei* | 11 | 2244 | 16015846 | 7137 | 55 | n.d. | 5 |
| TreXyn3 | *Trichoderma reesei* | 10 | 21487 | 141108772 | 6567 | 60 | 64 | 5.5 |
| TreXyn5 | *Trichoderma reesei* | 11 | 1410 | 8842816 | 6272 | 70 | 68 | 5 | n.d. = Not determined

WE-AX and WU-AX enzyme activities (U) were measured as described in sections "water extractable arabinoxylan (WE-AX) xylanase method" and "water un-extractable arabinoxylan (WU-AX) xylanase method".

Based on the results from the biochemical screening, xylanases having an appropriate activity ratio on soluble vs. insoluble arabinoxylan were choosen for further testing in application trials. The results are shown in table 3.

TABLE 3

Xylanases screened and the relative extract yield obtained using the xylanases versus a blank (without xylanases). Finally the xylanases substrate specificity is illustrated as a ration of their activity on insoluble vs. soluble arabinoxylan (WU-AX/WE-AX).

| Name | Origin | Filtration Performance | | | | WU-AX/ WE-AX |
|---|---|---|---|---|---|---|
| | | 5 min | 10 min | 15 min | 30 min | |
| Blank | | 1.00 | 1.00 | 1.00 | 1.00 | |
| BsuXyn3 | Bacillus subtilis, BS3 | 0.93 | 0.95 | 0.96 | 0.95 | 13388 |
| BsuXyn4 | Bacillus subtilis, BS4 #160 | n.d. | n.d. | n.d. | n.d. | 18619 |
| TerXyn1 | Geosmithia emersonii (Taleromyces emersonii) | 2.19 | 1.92 | 1.70 | 1.44 | 4232 |
| AtuXyn3 | Aspergillus tubigensis | 2.06 | 1.75 | 1.59 | 1.37 | 6361 |
| AtuXyn4 | Aspergillus tubigensis | 1.02 | 1.01 | 1.01 | 1.01 | 8084 |
| AacXyn2 | Aspergillus aculeatus | 2.07 | 1.86 | 1.67 | 1.43 | 4994 |
| TreXyn3 | Trichoderma reesei | 2.41 | 2.02 | 1.81 | 1.55 | 6567 |
| TreXyn5 | Trichoderma reesei | 2.06 | 1.75 | 1.59 | 1.37 | 6272 |

Filtration performance was measured as described earlier ("filtration"), and is presented as volume filtrate at the different time points relative to the negative control (blank).

WE-AX and WU-AX enzyme activities (U) were measured as described in sections "water extractable arabinoxylan (WE-AX) xylanase method" and "water un-extractable arabinoxylan (WU-AX) xylanase method".

Glucanases:

Glucanases were screened for their activity and temperature characteristics, and the results are shown in table 4.

TABLE 4

Glucanases screened, their activity and their biochemical characteristics in regard to temperature

| Name | Origin | U/ml | Temp opt, ° C. | T½ temp_ buffer, ° C. | T½ temp_ wort, ° C. | pH opt. |
|---|---|---|---|---|---|---|
| TerGlu1 | Talaromyces emersonii/ Geosmithia emersonii | 7338 | 70 | 78 | 78 | 3 |
| BsuGluS | Bacillus subtilis | 208 | 55-65 | 60 | 68 | 5-6 |
| BsuGlu103FULL | Bacillus subtilis | 391 | 50-60 | 53 | 58 | 5-6 |
| TreGlu2 | Trichoderma reesei | 13 | 40-50 | 70 | 74 | 4.5-6 |
| TreGlu3 | Trichoderma reesei | 9215 | 40-51 | 58 | 62 | 4.5-6 |
| TreGlu4 | Trichoderma reesei | n.d. | 40-52 | 62 | 62 | 4.5-6 |
| TreGlu6 | Trichoderma reesei | n.d. | 40-53 | 62 | 64 | 4.5-6 |
| TreGlu7 | Trichoderma reesei | n.d. | 40-54 | 62 | 62 | 4.5-6 |
| TreGlu8 | Trichoderma reesei | n.d. | 40-55 | 61 | 63 | 4.5-6 |
| BsuGluC CBD | Bacillus subtilis | 10 | 50-60 | 60 | 67 | 5-6 | n.d. = Not determined

Glucanase activity/units was/were determined as described in the glucanase activity assay as described above.

Based on the results from the biochemical screening, glucanases having suitable characteristics were chosen for further testing in application trials. The results are shown in table 5.

TABLE 5

Name and origin of glucanases screened and the relative extract yield obtained using the glucanases versus a blank (without enzyme).

| Name | Origin | Filtration performance | | | |
|---|---|---|---|---|---|
| | | 5 min | 10 min | 15 min | 30 min |
| Blank | Neg control | 1.00 | 1.00 | 1.00 | 1.00 |
| TerGlu1 | Geosmithia emersonii | 1.36 | 1.43 | 1.46 | 1.36 |
| BsuGluS | Bacillus subtilis | 1.48 | 1.49 | 1.48 | 1.35 |
| BsuGlu103FULL | Bacillus subtilis | 1.29 | 1.28 | 1.30 | 1.22 |
| TreGlu2 | Trichoderma reesei | 1.15 | 1.18 | 1.20 | 1.15 |
| TreGlu3 | Trichoderma reesei | 1.29 | 1.32 | 1.30 | 1.22 |
| TreGlu4 | Trichoderma reesei | 1.11 | 1.11 | 1.11 | 1.09 |
| TreGlu6 | Trichoderma reesei | 1.13 | 1.15 | 1.13 | 1.10 |
| TreGlu7 | Trichoderma reesei | 1.06 | n.d. | 1.01 | 1.02 |
| TreGlu8 | Trichoderma reesei | 1.12 | 1.11 | 1.13 | 1.09 |
| BsuGluC CBD | Bacillus subtilis | 1.33 | 1.37 | 1.37 | 1.32 |

Filtration performance was measured as described earlier ("filtration"), and is presented as volume filtrate at the different time points relative to the negative control (blank).

Based on the individual screening of xylanases and glucanases, combinatorial experiments were conducted, and results are illustrated in table 6.

TABLE 6

Brewing application results from combinatorial experiments of xylanases and glucanases versus a blank and versus UltraFlo ® Max. 250 Fungal Xylanase Units FXU-S/g; 700 Cellulase Units EGU/g (Novozymes, Denmark) results are illustrated as relative extract yield obtained.

| Name | Origin | Filtration performance | | | |
|---|---|---|---|---|---|
| | | 5 min | 10 min | 15 min | 30 min |
| Control | | 1.00 | 1.00 | 1.00 | 1.00 |
| UFmax 0.1 | A. aculeatus | 2.29 | 2.13 | 2.00 | 1.77 |
| BsuGluS/ TauXyn1 | B. sub/T. aurantiacus | 1.70 | 1.69 | 1.60 | 1.47 |
| BsuGluS/ AtuXyn3 | B. sub/A. tubingensis | 2.57 | 2.14 | 1.96 | 1.75 |

(Origin of UltraFlo® Max may include other microorganisms than *A. aculeatus*, such as described in WO05059084)

Filtration performance was measured as described earlier ("filtration"), and is presented as volume filtrate at the different time points relative to the negative control (blank).

Suitable combinations were further tested in a 2HL pilot scale facility for verification, and results are shown in table 7 and FIG. 3.

TABLE 7

Pilot scale Brewing application results from verification of the glucanase and xylanases screening. The *B. sub* glucanase S combined with the *A. tub* xylanases were tested against a blank and UltraFlo ® Max. Data collected was the average flow (L/h), the total pressure build up over the lautering (mm WC) and the max pressure recorded during the lautering (mm WC).

| ID | Avg Flow (L/h) | Total pressure build up (mm WC) | Max pressure (mm WC) |
|---|---|---|---|
| Blank | 148 | 556 | 356 |
| UltraFlo max | 149 | 478 | 280 |
| BsuGluS/AtuXyn3 | 147 | 263 | 163 |

Example 2

In this example it was attempted to show that xylanases for brewing applications may have a very high selectivity for High Molecular Weight Soluble-arabinoxylan (HMWS-AX) and water extractable arabinoxylan (WE-AX). It is believed that hereby only limited amounts of arabinoxylan need to be solubilised. Consequently, the related off flavour potential is highly reduced.

A significantly reduced viscosity is facilitating mash and beer separation. Desired xylanase characteristics for brewing applications may include one or more of the following aspects of table 8:

TABLE 8

Screening criterias for xylanase selection

Enzyme substrate specificity
WE-AX/WU-AX ratio has an impact on viscosity
Enzyme substrate selectivity
How close to branch points the enzyme will cut has an impact on the functionality
Enzyme thermostability
Continuous solubilisation of AX during mashing - thermostability is a key feature
Enzyme pH optimum (pH 5.4-5.6)
Enzyme inhibition (e.g. known key factor for xylanases)

TABLE 9

Xylanases - biochem characteristics
Inhibition by endogenous cereal xylanase inhibitors occur in both xylanase GH's

| Xylanase GH | GH10 | GH11 |
|---|---|---|
| Mw | +30 kDa | 20 kDa |
| Substrate specificity | Hydrolyse close to Arabinose substitutions | Need more unsubstituted Xylose to hydrolyse AX |
| Substrate selectivity | WE-AX/WU-AX typically >1 | WE-AX/WU-AX typically <1 |
| SBD | Often separate SBD | No classical SBD, but secondary BD on surface |
| Technological effect | Viscosity reducers | Solubilizer/ viscosity reducers |

Water-Unsoluble ArabinoXylan (WU-AX) in cereals as shown in FIG. 3 is linked to filter cake stability in the brew house.

The concentration of ferulic acid (FA) in cereals very much depends on the tissue. The highest concentration is found in the pericarp material, whereas the concentration in the endosperm is much lower. Different concentrations are reported. A concentration of 2700 µg/g insoluble fiber, 185 µg/g soluble fiber is likely (Bunzel et al. 2001, Journal of Sc. of food and agriculture, vol. 81, p. 653-60).

To put this into perspective it means that FA is only found for every 200th xylose molecules in arabinoxylan in insoluble fiber (WU-AX) and for every 2500 xylose in soluble fiber (WE-AX).

It is a well-known fact that xylanases may lead to off-flavor formation in beer such as free ferulic acid and 4-VG.

Methods:

Based on the criteria mentioned in table 8+9 more than 15 xylanases from DuPont Industrial Biosciences were found as potential candidates. The xylanases were screened in laboratory mashing application applying up to 30% barley in combination with malt. Among others, mash separation speed; pentosan/arabinoxylan level and wort viscosities were monitored. Top candidates where tested at several pilot brewery plant studies to test our hypothesis and link xylanase characteristics to functionality in brewing. The optimal dosage of the selected xylanase candidate was tested in combination with a 8-glucanase.

Results and Discussion:

TABLE 10

| Sample ID | Control | Ref (X + B) | X1 | X2 | X3 |
|---|---|---|---|---|---|
| Dyn. Viscosity (12 °Plato) mPa · s | 1.798 | 1.670 | 1.801 | 1.746 | 1.794 |
| Extract (°Plato) | 15.1 | 15.7 | 15.6 | 15.2 | 15.1 |
| Total pentosan (mg/l) | 1610 | 1910 | 2440 | 2020 | 1710 |

Pilot plant brews where enzyme dosage is the only variable. Applying a WU-AX selective xylanase (X1) results in filter bed collapse. WE-AX selective xylanase candidates (reference, X2, X3) results in low pressure buildup. The reference is a blend of xylanase+beta-glucanase.

TABLE 11

Wort analyses - pilot plant studies

| Sample ID | Ref. | X + B | Xh + B |
|---|---|---|---|
| Extract (°Plato) | 15.70 | 16.00 | 15.95 |
| Betaglucan in wort (mg/l) | 44 | 35 | 25 |
| Dyn. Viscosity at 12 °Plato (mPa · s) | 1.65 | 1.68 | 1.68 |
| Total pentosan (mg/l) | 3540 | 2970 | 3010 |

TABLE 12

Strecker Aldehyd analysis of aged beer

| Aging markers (forced aged beer) | Unit | Ref. | X + B | Xh + B |
|---|---|---|---|---|
| 2-Me—Pr | ppb | 25 | 24 | 22 |
| 2-Me—Bu | ppb | 3 | 2 | 3 |
| 3-Me—Bu | ppb | 9 | 7 | 8 |
| Furfural | ppb | 113 | 85 | 93 |
| Methional | ppb | 6 | 5 | 6 |
| PheAcal | ppb | 10 | 9 | 10 |
| T2N | ppb | 0.022 | 0.022 | 0.022 |

Optimized blends of a WE-AX selective xylanase applied at a medium (X) and a high dosage (Xh) in combination with β-glucanase (B) on 20% barley/80% malt. The results indicate a good mash and beer separation performance with a low risk of off-flavor formation and filter bed collapse.

Conclusion:

The study has proven the importance of applying xylanases for brewing which are highly selective for the WE-AX during mashing. The following benefits are achieved:

Good mash separation and beer filtration performance
Minimized risk of filter bed collapse at lautering
Reduced potential for off-flavor formation related to arabinoxylan breakdown
Tolerance towards xylanase overdose Xylanases can often be applied with a high beneficial effect in combination with beta-glucanases for separation control.

Example 3

Evaluation of X3/BgIS (Also Referred to as AtuXyn3/BsuGluS) Combinations in 2 HL Pilot Brewing Trials Material and Methods:
Experiments: Enzymes:

AtuXyn3 (X3)/BsuGluS (Bgls) (a): Combination of BgIS (*Bacillus glucanase*) and X3 (*Aspergillus xylanase*; BgLS: 0.50 mg protein/kg grist and X3: 1.50 mg protein/kg grist).

AtuXyn3 (X3)/BsuGluS (Bgls) (b): As AtuXyn3 (X3)/BsuGluS (Bgls) (a), but with 20% increase X3 dose to test robustness.

Reference: Benchmark enzyme product (Ultraflo® Max) dosed at 0.20 kg/T grist.

Raw Material:

Adjunct material: barley. 22% w/w.

Malt: Pilsner malt Chiraz 42,6% w/w, Pilsner malt Quench DMG 35,4% weight pr. weight (ww).

All material used for acid adjustment of pH, Calcium, Zink and bitterness levels are food grade and considered as standard brewing materials.

The recipe for the brew was aiming at a beer style as an international lager beer.

Milling:

Künzel 2 roller pilot mill. The milled material was passing the rollers twice simulating a 4 roller mill.

Malt grist: the mill was running at 1.5 mm at the first pass and 0.7 mm at the second pass of the rollers.

Barley grist: the mill was running at 1.5 mm at the first pass and 0.4 mm at the second pass of the rollers.

Brewhouse 2 HL:

All brews were based on HGB (High Gravity Brewing) infusion mashing and standard lautering of 190 L wort aiming at 16° Plato. During lautering which was performed at fixed flow, the differential pressure was recorded (used as parameter for evaluating lautering performance). All brew materials were milled ahead of time (24 h) and kept in closed buckets prior to water contact. All material was dumped in the mash kettle within the first 3 minutes after start of mashing. Calcium and pH adjustment were done prior to enzyme addition. pH (20° C.) was rechecked at the 52° C. break. Iodine normality was confirmed after 10 minutes at 72° C. Lautering was performed at 78° C.

Lautering performance was evaluated on fixed flow at 90 l/H during first wort collection. Flow was increased to 110 L/hour and 130 L/hour during sparging and weak wort collection. Chemical analysis was performed on cold wort.

Wort Boiling:

Boiling was performed using an external boiler with 4-5% evaporation. Hop extracts were added from the beginning of the wort boiling aiming at 20 BU in the final beer.

Fermentation 50 L:

All fermentations were performed in 50 L cylindriconical tanks. Fermentation was made according to standard operation procedures. Pitching was done with $15 \times 10^6$ live yeast cells/ml. Yeast counts and viability was, calculated using a Nucleo counter.

Beer Processing:

Plate and frame filter operated at constant pressure. Flow evaluation was done by weight.

Data was collected from 1 and 3 filter plates.

Debrewing:

All beers were de-brewed to 5.0% ABV (Alcohol By Volume), considered as international lager beer standard.

Bottling:

$CO_2$ was adjusted to 5.0 g/L. All beer samples were bottled in 33 cl standard bottles on a McLennon automatic filling machine using single evacuation.

Beer Analysis:

Fresh beers were analysed using GC-MS

Chemical aging profile was determined using GC-MS.

Results and observations: Mashing.

Mashing was performed with the following condition:

52° C. for 10 minutes simulating a 15-20 minutes mashing using a running mill.

65° C. for 40 minutes.

72° C. for 30 minutes.

78° C. for 10 minutes.

All ramping steps were executed at 1° C. A graphic representation is given in FIG. 7.

All trials were made with this mashing regime aiming at a 16° Plato. brew. There were no remarks to this process step.

Results and observations: Lautering.

The lautering was performed in the 2 hl brewery with a load of 150 kg/m². This is representative for a standard brew house operation. Control of the lautering process was made as a fixed flow at an average of 100 liter/hour. Initial flow rate is 90 liter/hour, increasing to 130 liter/hour during weak wort collection. Differential pressure and in-line measurement of haze was recorded for the four brews. Total lautering and wort collection Was done over approximately 2 hours.

Trial X3/BgIS (b) and X3/BgIS (a) are suggested to be the trials that had the best lautering performance followed by trial X3/BgIS (a) and trial UF max with the worst performance.

TABLE 13

Data collected during lautering of the mash from the four trials.

|  | UF max | X3/BglS (a) | X3/BglS (b) | X3/BglS (a) |
|---|---|---|---|---|
| Lauter tun load (kg/m3) | 153 | 153 | 153 | 153 |
| Lauter tun time (min) | 154 | 164 | 170 | 154 |
| Diff. Pressure (cm) | 40 | 30 | 30 | 30 |
| Racking (# deep cuts) | 1 | 1 | 1 | 1 |
| Haze (EBC) | 10 | 15 | 10 | 10 |
| First wort pressure build up (cm/h) | 40 | 33 | 31 | 30 |
| Time to first deep cut (min) | 45 | 60 | 120 | 115 |

"Diff. Pressure" and "First wort pressure build up" in the table was measured as cmWC (cm Water column) and not as (cm) and (cm/h) respectively.

Results and observations: Wort analysis after boiling.

Analysis of the cold wort shows similar results. The beta-glucan analysis indicates a slight difference between the samples.

TABLE 14

Chemical analysis of the cold wort.

| Wort | UF max | X3/BglS (a) | X3/BglS (b) | X3/BglS (a) |
|---|---|---|---|---|
| Extract (% plato) | 16.09 | 16.05 | 15.99 | 16.1 |
| Color (EBC) | 9.7 | 9.3 | 9.3 | 9.3 |
| pH | 5 | 5.2 | 5.2 | 5.2 |

TABLE 14-continued

Chemical analysis of the cold wort.

| Wort | UF max | X3/BglS (a) | X3/BglS (b) | X3/BglS (a) |
|---|---|---|---|---|
| Iodine (Y/N) | N | N | N | N |
| Bitterness (BU, EBC) | 52 | 51 | 46 | 50 |

TABLE 15

Analytical data on cold wort.

|  | UF max | X3/BglS (a) | X3/BglS (b) | X3/BglS (a) |
|---|---|---|---|---|
| Beta-glucan in wort (mg/L) | 49 | 40 | 25 | 30 |
| Dyn. Viscosity at 12° C. (mPa · s) | 1,888 | 1,685 | 1,679 | 1,686 |
| Pentosan (mg/l) | 3365 | 2975 | 3014 | 2964 |
| Ferulic acid (ug/ml) | 4.3 | 3.9 | 3.8 | 3.9 |
| 4-VG (ug/ml) | <0.49 | <0.49 | <0.49 | <0.49 |

(12° C. is 12 °Plato);
(% Plato may be used interchangeably with °Plato)

Results and observations: Fermentation.

Analysis of the green beer is given in table 16.

TABLE 16

Green beer analysis.

| Green beer | UF max | X3/BglS (a) | X3/BglS (b) | X3/BglS (a) |
|---|---|---|---|---|
| Alcohol (% vol) | 6.79 | 6.79 | 6.7 | 6.86 |
| Real extract (% P) | 6.28 | 6 | 6 | 6 |
| RDF (%) | 63.5 | 63.7 | 63.5 | 64.4 |
| Original extract (% P) | 16.29 | 16.25 | 16.09 | 16.24 |
| Color (EBC) | 8.3 | 8.5 | — | — |
| pH | 4.4 | 4.4 | 4.4 | 4.4 |
| SO2 (ppm) | 7 | 9 | 11 | 10 |
| Bitterness (BU, EBC) | 29 | 28 | 27 | 27 |

The green beer analysis shows a high degree of similarity between the trials. All trials have relative low RDF; but this is normally seen with the inclusion of 22% barley calculated on the basis of weight per weight (ww).

Results and observations: Beer filtration.

Beer samples were filtered using a plate and frame filter using a fixed pressure. Two kegs of approximately 15 kg were filtered and the individual keg filtration data are presented in table 17. The first keg was filtered using 1 filter sheet and the second keg was filtered using 3 filter sheets. The differential pressure was always 0.5 bar. The filter plates are KD7 (20 cmx20 cm) from Begerow.

The overall picture of the filtrations curves from either 1 or 3 filter plate filtrations is the same. We believe that the 1 filter plate record may be too sensitive to show the real ratio difference.

TABLE 17

Keg filtration data from the four trials

| Filtration | UF max | X3/BglS (a) | X3/BglS (b) | X3/BglS (a) |
|---|---|---|---|---|
| Filtration speed - 1 filter sheet (L/h) | 4.8 | 5.6 | 9.9 | 11.8 |
| Filtration speed - 3 filter sheet (L/h) | 77.2 | 59.6 | 70.6 | 105.4 |

Results and observations: Final beer analysis.

Trial beers were analysed according to standard operation procedures (EBC) and presented in table 18.

TABLE 18

Final beer analysis.

| Finished beer | UF max | X3/BglS (a) | X3/BglS (b) | X3/BglS (a) |
|---|---|---|---|---|
| alcohol (%) | 4.82 | 4.89 | 5.01 | 4.92 |
| Real extract (% P) | 4.5 | 4.6 | 4.6 | 4.4 |
| RDF (%) | 63.2 | 63.4 | 63.8 | 64.3 |
| Original extract (% P) | 11.85 | 11.99 | 12.19 | 11.89 |
| Color (EBC) | 4.8 | 4.9 | 5 | 5 |
| pH | 4.4 | 4.4 | 4.4 | 4.4 |
| SO2 (ppm) | 13 | 13 | 10 | 6 |
| Bitterness (BU, EBC) | 22 | 22 | 20 | 18 |
| Haze (EBC) | 0.43 | 0.4 | 0.38 | 0.4 |
| Total haze - 5 d-60 dg C. (EBC) | 8.6 | 12.9 | 7.3 | 6.2 |
| CO2 (g/L) | 4.9 | 5.3 | 5.1 | 5.2 |
| Diacetyl (ppb) | 12 | 11 | 8 | 10 |
| Head retention (S) | 107 | 111 | 119 | 108 |
| Foam volume (ml) | 452 | 476 | 460 | 470 |

Results and observations: Strecker aldehydes and "age markers" in final beer.

Analysis was performed both on fresh and aged beer. Strecker aldehydes and the "age and heat markers" (2-Me-Pr (2-methyl Propanal), 2-Me-Bu (2-methyl Butanal), 3-Me-Bu (3-methyl Butanal), Furfural, Methional, PheAcal (phenyl Acetaldehyde) and T2N (trans-2-nonenal)) were analysed by GC-MS on both fresh and aged beer. The data from analysis of fresh beer is presented in table 19.

TABLE 19

Strecker aldehyde analysis of fresh beer. Markers for heat and aging (Furfural and trans-2-Nonenal) are used as sample control.

| Aging markers (fresh beer) | UF max | X3/BglS (a) | X3/BglS (b) | X3/BglS (a) |
|---|---|---|---|---|
| 2-ME-Pr (ppb) | 5 | 5 | 5 | 6 |
| 2-ME-Bu (ppb) | 2 | 2 | 2 | 2 |
| 3-ME-Bu (ppb) | 6 | 6 | 6 | 6 |
| Furfural (ppb) | 10 | 11 | 11 | 10 |
| Methional (ppb) | 4 | 4 | 4 | 4 |
| PheAcal (ppb) | 6 | 6 | 6 | 7 |
| T2N (ppb) | 0.0011 | 0.005 | 0.004 | 0.006 |

The trial beers were incubated at 37° C. for 2 weeks prior to the Strecker aldehyde analysis. The data for aged beer samples are presented in table 20.

TABLE 20

Strecker aldehyde analysis of aged beer. Markers for heat and aging (furfural and trans-2-Nonenal) is used as a sample control.

| Aging markers (forced aged beer) | UF max | X3/BglS (a) | X3/BglS (b) | X3/BglS (a) |
|---|---|---|---|---|
| 2-ME-Pr (ppb) | 25 | 23 | 22 | 26 |
| 2-ME-Bu (ppb) | 3 | 3 | 3 | 2 |
| 3-ME-Bu (ppb) | 9 | 7 | 7 | 8 |
| Furfural (ppb) | 111 | 92 | 93 | 78 |
| Methional (ppb) | 6 | 5 | 6 | 6 |
| PheAcal (ppb) | 10 | 9 | 9 | 10 |
| T2N (ppb) | 0.017 | 0.022 | 0.022 | 0.022 |

The data presented in table 20 show an expected increase in Strecker aldehyde level. The increase in furfural and trans-2-Nonenal reach an expected level.

Conclusion:

Based on the pilot scale experiments, we, can conclude that the ratios of the BglS and X3 tested in this Experiment performs as good or even better than the reference UltraFlo Max in pilot scale brewing.

The results are surprising, seen in the light of the challenging rawmaterial used, 22% barley inclusion in combination with the 300 mg/l β-glucan containing malt. The performance is not only seen in the mash separation results, also in the beer filtration. Due to the low solubilisation of cell wall material when using the BREW2 (pentosan data), a lower degree of cell wall material that might cause quality issues in relation to off-taste and stability, can be recorded.

Finally it can be concluded that a 20% increase in the dose of the xylanase component in X3/Bgls (b) appears not to have any impact on any of the evaluated parameters, indicating that X3/Bgls (a) is a robust enzyme combination.

```
Sequences:
AtuXyn3, Aspergillus tubigensis, 302 aa
                                      (SEQ ID NO: 1)
QASVSIDTKFKAHGKKYLGNIGDQYTLTKNSKTPAIIKADFGA

LTPENSMKWDATEPSRGQFSFSGSDYLVNFAQSNNKLIRGHTL

VWHSQLPSWVQAITDKNTLIEVMKNHITTVMQHYKGKIYAWDV

VNEIFNEDGSLRDSVFYQVIGEDYVRIAFETARAADPNAKLYI

NDYNLDSASYPKLTGMVSHVKKWIEAGIPIDGIGSQTHLSAGG

GAGISGALNALAGAGTKEIAVTELDIAGASSIDYVEVVEACLD

QPKCIGITVWGVADPDSWRSSSTPLLFDSNYNPKPAYTAIANAL

TerXyn1, Geosmithia emersonii
(Taleromyces emersonii)
                                      (SEQ ID NO: 2)
AGLNTAAKAIGLKYFGTATDNPELSDTAYETQLNNTQDFGQLTP

ANSMKWDATEPEQNVFTFSAGDQIANLAKANGQMLRCHNLVWYN

QLPSWVTSGSWTNETLLAAMKNHITNVVTHYKGQCYAWDVVNEA

LNDDGTYRSNVFYQYIGEAYIPIAFATAAAADPNAKLYYNDYNI

EYPGAKATAAQNLVKLVQSYGARIDGVGLQSHFIVGETPSTSSQ

QQNMAAFTALGVEVAITELDIRMQLPETEALLTQQATDYQSTVQ

ACANTKGCVGITVWDWTDKYSWVPSTFSGYGDACPWDANYQKKP

AYEGILTGLGQTVTSTTYIISPTTSVGTGTTTSSGGSGGTTGVA

QHWEQCGGLGWTGPTVCASGYTCTVINEYYSQCL

AtuXyn4, Aspergillus tubigensis
                                      (SEQ ID NO: 3)
EPIEPRQASVSIDTKFKAHGKKYLGNIGDQYTLTKNSKTPAIIK

ADFGALTPENSMKWDATEPSRGQFSFSGSDYLVNFAQSNNKLIR

GHTLVWHSQLPSWVQSITDKNTLIEVMKNHITTVMQHYKGKIYA

WDVVNEIFNEDGSLRDSVFYKVIGEDYVRIAFETARAADPNAKL

YINDYNLDSASYPKLTGMVSHVKKWIAAGIPIDGIGSQTHLSAG

GGAGISGALNALAGAGTKEIAVTELDIAGASSTDYVEVVEACLN

QPKCIGITVWGVADPDSWRSSSTPLLFDSNYNPKPAYTAIANAL
```

-continued

AacXyn2, *Aspergillus aculeatus*
(SEQ ID NO: 4)
MVGLLSITAALAATVLPNIVSAVGLDQAAVAKGLQYFGTATDNP

ELTDIPYVTQLNNTADFGQITPGNSMKWDATEPSQGTFTFTKGD

VIADLAEGNGQYLRCHTLVWYNQLPSWVTSGTWTNATLTAALKN

HITNVVSHYKGKCLHWDVVNEALNDDGTYRTNIFYTTIGEAYIP

IAFAAAAAADPDAKLFYNDYNLEYGGAKAASARAIVQLVKNAGA

KIDGVGLQAHFSVGTVPSTSSLVSVLQSFTALGVEVAYTEADVR

ILLPTTATTLAQQSSDFQALVQSCVQTTGCVGFTIWDWTDKYSW

VPSTFSGYGAALPWDENLVKKPAYNGLLAGMGVTVTTTTTTTA

TATGKTTTTTTGATSTGTTAAHWGQCGGLNWSGPTACATGYTCT

YVNDYYSQCL

TreXyn3, *Trichoderma reesei*
(SEQ ID NO: 5)
MKANVILCLLAPLVAALPTETIHLDPELAALRANLTERTADLWD

RQASQSIDQLIKRKGKLYFGTATDRGLLQREKNAAIIQADLGQV

TPENSMKWQSLENNQGQLNWGDADYLVNFAQQNGKSIRGHTLIW

HSQLPAWVNNINNADTLRQVIRTHVSTVVGRYKGKIRAWDVVNE

IFNEDGTLRSSVFSRLLGEEFVSIAFRAARDADPSARLYINDYN

LDRANYGKVNGLKTYVSKWISQGVPIDGIGSQSHLSGGGGSGTL

GALQQLATVPVTELAITELDIQGAPTTDYTQVVQACLSVSKCVG

ITVWGISDKDSWRASTNPLLFDANFNPKPAYNSIVGILQ

TreXyn5, *Trichoderma reesei*
(SEQ ID NO: 6)
QCIQPGTGYNNGYFYSYWNDGHGGVTYCNGPGGQFSVNWSNSGN

FVGGKGWQPGTKNRVINFSGSYNPNGNSYLSVYGWSRNPLIEYY

IVENFGTYNPSTGATKLGEVTSDGSVYDIYRTQRVNQPSIIGTA

TFYQYWSVRRNHRSSGSVNTANHFNAWAQQGLTLGTMDYQIVAV

EGYFSSGSASITVSD

BsuGluS, *Bacillus subtilis*, 214 aa
(SEQ ID NO: 7)
QTGGSFFDPFNGYNSGFWQKADGYSNGNMFNCTWRANNVSMTSL

GEMRLALTSPAYNKFDCGENRSVQTYGYGLYEVRMKPAKNTGIV

SSFFTYTGPTDGTPWDEIDIEFLGKDTTKVQFNYYTNGAGNHEK

IVDLGFDAANAYHTYAFDWQPNSIKWYVDGQLKHTATNQIPTTP

GKIMMNLWNGTGVDEWLGSYNGVNPLYAHYDWVRYTKK

TerGlu1, *Geosmithia emersonii*
(*Taleromyces emersonii*)
(SEQ ID NO: 8)
APVKEKGIKKRASPFQWFGSNESGAEFGNNNIPGVEGTDYTFPN

TSAIQILIDQGMNIFRVPFLMERMVPNQMTGPVDSAYFQGYSQV

INYITSHGASAVIDPHNFGRYYNNIISSPSDFQTFWHTIASNFA

DNDNVIFDTNNEYHDMDESLVVQLNQAAIDGIRAAGATSQYIFV

EGNSWTGAWTWTQVNDAMANLTDPQNKIVYEMHQYLDSDGSGTS

DQCVNSTIGQDRVESATAWLKQNGKKAILGEYAGGANSVCETAV

TGMLDYLANNTDVWTGAIWWAAGPWWGDYIFSMEPPSGIAYEQV

LPLLQPYL

BsuGlu103FULL, *Bacillus subtilis*
(SEQ ID NO: 9)
DDYSVVEEHGQLSISNGELVNERGEQVQLKGMSSHGLQWYGQFV

NYESMKWLRDDWGITVFRAAMYTSSGGYIDDPSVKEKVKETVEA

AIDLGIYVIIDWHILSDNDPNIYKEEAKDFFDEMSELYGDYPNV

IYEIANEPNGSDVTWDNQIKPYAEEVIPVIRDNDPNNIVIVGTG

TWSQDVHHAADNQLADPNVMYAFHFYAGTHGQNLRDQVDYALDQ

GAAIFVSEWGTSAATGDGGVFLDEAQVWIDFMDERNLSWANWSL

THKDESSAALMPGANPTGGWTEAELSPSGTFVREKIRESASIPP

SDPTPPSDPGEPDPGEPDPTPPSDPGEYPAWDSNQIYTNEIVYH

NGQLWQAKWWTQNQEPGDPYGPWEPLKSDPDSGEPDPTPPSDPG

EYPAWDSNQIYTNEIVYHNGQLWQAKWWTQNQEPGDPYGPWEPLN

TreGlu2, *Trichoderma reesei*
(SEQ ID NO: 10)
QQTVWGQCGGIGWSGPTNCAPGSACSTLNPYYAQCIPGATTITT

STRPPSGPTTTTRATSTSSSTPPTSSGVRFAGVNIAGFDFGCTT

DGTCVTSKVYPPLKNFTGSNNYPDGIGQMQHFVNDDGMTIFRLP

VGWQYLVNNNLGGNLDSTSISKYDQLVQGCLSLGAYCIVDIHNY

ARWNGGIIGQGGPTNAQFTSLWSQLASKYASQSRVWFGIMNEPH

DVNINTWAATVQEVVTAIRNAGATSQFISLPGNDWQSAGAFISD

GSAAALSQVTNPDGSTTNLIFDVHKYLDSDNSGTHAECTTNNID

GAFSPLATWLRQNNRQAILTETGGGNVQSCIQDMCQQIQYLNQN

SDVYLGYVGWGAGSFDSTYVLTETPTGSGNSWTDTSLVSSCLARK

TreGlu3, *Trichoderma reesei*
(SEQ ID NO: 11)
QTSCDQWATFTGNGYTVSNNLWGASAGSGFGCVTAVSLSGGASW

HADWQWSGGQNNVKSYQNSQIAIPQKRTVNSISSMPTTASWSYS

GSNIRANVAYDLFTAANPNHVTYSGDYELMIWLGKYGDIGPIGS

SQGTVNVGGQSWTLYYGYNGAMQVYSFVAQINTTNYSGDVKNFF

NYLRDNKGYNAAGQYVLSYQFGTEPFTGSGTLNVASWTASIN

TreGlu4, *Trichoderma reesei*
(SEQ ID NO: 12)
HGHINDIVINGVWYQAYDPTTFPYESNPPIVVGWTAADLDNGFV

SPDAYQNPDIICHKNATNAKGHASVKAGDTILFQWVPVPWPHPG

PIVDYLANCNGDCETVDKTTLEFFKIDGVGLLSGGDPGTWASDV

LISNNNTWVVKIPDNLAPGNYVLRHEIIALHSAGQANGAQNYPQ

CFNIAVSGSGSLQPSGVLGTDLYHATDPGVLINIYTSPLNYMPG

PTVVSGLPTSVAQGSSAATATASATVPGGGSGPTSRTTTTARTT

QASSRPSSTPPATTSAPAGGPTQTLYGQCGGSGYSGPTRCAPPA

TCSTNPYYAQCLN

TreGLu6, Trichoderma reesei
(SEQ ID NO: 13)
AFSWKNVKLGGGGGFVPGIIFHPKTKGVAYARTDIGGLYRLNAD

DSWTAVTDGIADNAGWHNWGIDAVALDPQDDQKVYAAVGMYTNS

WDPSNGAIIRSSDRGATWSFTNLPFKVGGNMPGRGAGERLAVDP

ANSNITYFGARSGNGLWKSTDGGVTFSKVSSFTATGTYIPDPSD

SNGYNSDKQGLMWVTFDSTSSTTGGATSRIFVGTADNITASVYV

STNAGSTWSAVPGQPGKYFPHKAKLQPAEKALYLTYSWWPDAQL

FRSTDGTTWSPIWAWASYPTETYYYSISTPKAPWIKNNFIDVT

SESPSDGLIKRLGWMIESLEIDPTDSNHWLYGTGMTIFGGHDLT

NWDTRHNVSIQSLADGIEEFSVQDLASAPGGSELLAAVGDDNGF

TFASANDLGTSPQTVWATPTWATSTSVDYAGNSVKSVVRVGNTA

GTQQVAISSDGGATWSIDYAADTSMNGGTVAYSADGDTILWSTA

SSGVQRSQFQGSFASVSSLPAGAVIASDKKTNSVFYAGSGSTFY

VSKDTGSSFTRGPKLGSAGTIRDIAAHPTTAGTLYVSTDVGIFR

STDSGTTFGQVSTALTNTYQIALGVGSGSNWNLYAFGTGPSGAR

LYASGDSGASWTDIQGSQGFGSIDSTKVAGSGSTAGQVYVGTNG

RGVFYAQGTVGGGTGGTSSSTKQSSSSTSSASSSTTLRSSVVST

TRASTVTSSRTSSAAGPTGSGVAGHYAQCGGIGWTGPTQCVAPY

VCQKQNDYYYQCV

TreGLu7, Trichoderma reesei
(SEQ ID NO: 14)
HGQVQNFTINGQYNQGFILDYYYQKQNTGHFPNVAGWYAEDLDL

GFISPDQYTTPDIVCHKNAAPGAISATAAAGSNIVFQWGPGVWP

HPYGPIVTYVVECSGSCTTVNKNNLRWVKIQEAGINYNTQVWAQ

QDLINQGNKWTVKIPSSLRPGNYVFRHELLAAHGASSANGMQNY

PQCVNNIAVTGSGTKALPAGTPATQLYKPTDPGILFNPYTTITS

YTIPGP

ALWQG

TreGLu8, Trichoderma reesei
(SEQ ID NO: 15)
GKIKYLGVAIPGIDFGCDIDGSCPTDTSSVPLLSYKGGDGAGQM

KHFAEDDGLNVFRISATWQFVLNNTVDGKLDELNWGSYNKVVNA

CLETGAYCMIDMHNFARYNGGIIGQGGVSDDIFVDLWVQIAKYY

EDNDKIIFGLMNEPHDLDIEIWAQTCQKVVTAIRKAGATSQMIL

LPGTNFASVETYVSTGSAEALGKITNPDGSTDLLYFDVHKYLDI

NNSGSHAECTTDNVDAFNDFADWLRQNKRQAIISETGASMEPSC

MTAFCAQNKAISENSDVYIGFVGWGAGSFDTSYILTLTPLGKPG

NYTDNKLMNECILDQFTLDEKYRPTPTSISTAAEETATATATSD

GDAPSTTKPIFREETASPTPNAVTKPSPDTSDSSDDDKDSAASM

SAQGLTGTVLFTVAALGYMLVAF

BsuGLuC CBD, Bacillus subtilis
(SEQ ID NO: 16)
MKRSISIFITCLLITLLTMGGMIASPASAAGTKTPVAKNGQLSI

KGTQLVNRDGKAVQLKGISSHGLQWYGEYVNKDSLKWLRDDWG

ITVFRAAMYTADGGYIDNPSVKNKVKEAVEAAKELGIYVIIDW

HILNDGNPNQNKEKAKEFFKEMSSLYGNTPNVIYEIANEPNGD

VNWKRDIKPYAEEVISVIRKNDPDNIIIVGTGTWSQDVNDAAD

DQLKDANVMYALHFYAGTHGQFLRDKANYALSKGAPIFVTEWG

TSDASGNGGVFLDQSREWLKYLDSKTISWVNWNLSDKQESSSA

LKPGASKTGGWRLSDLSASGTFVRENILGTKDSTKDIPETPSK

LKPGASKTGGWRLSDLSASGTFVPQLQIKNNGNTTVDLKDVTA

RYWYKAKNKGQNFDCDYAQIGCGNVTHKFVTLHKPKQGADTYL

ELGFKNGTLAPGASTGNIQLRLHNDDWSNYAQSGDYSFFKSNT

FKTTKKITLYDQGKLIWGTEPN

BsuXyn3, Bacillus subtilis xylanase variant
(SEQ ID NO: 17)
ASTDYWQNWTFGGGIVNAVNGSGGNYSVNWSNTGNFVVGKWTT

GSPFRTINYNAGVWAPNGNGYLTLYGWTRSPLIEYYVVDSWGTY

RPTGTYKGTVKSDGGTYDIYTTTRYNAPSIDGDDTTFTQYWSVR

QSKRPTGSNATITFSNHVNAWKSHGMNLGSNWAYQVMATEGYQS

SGSSNVTVW

BsuXyn4, Bacillus subtilis xylanase variant
(SEQ ID NO: 18)
ASTDYWQNWTDGYGIVNAVNGSGGNYSVNWSNTGNFVVGKWTT

GSPFRTINYNAGVWAPNGNGYLTLYGWTRSPLIEYYVVDSWGTY

RPTGTYKGTVYSDGGWYDIYTATRDNAPSIDGDFTTFTQYWSVR

QSKRPTGSNATITFSNHVNAWRSHGMDLGSNWAYQVMATEGYLS

SGSSNVTVW

---

The invention claimed is:

1. A product selected from the group consisting of a food, a beverage, a feed, a paper product, a pulp product, and a biofuel wherein the product comprises:
   a first enzyme exhibiting endo-1,4-β-xylanase activity, said first enzyme having the amino acid sequence of SEQ ID NO:1; and
   a second enzyme exhibiting endo-1,3(4)-β-glucanase activity, said second enzyme having the amino acid sequence of SEQ ID NO:7.

2. The product according to claim 1, further comprising at least one additional component chosen from the group consisting of an enzyme carrier, a stabilizer, and a preservative.

3. The product according to claim 1, wherein the product has a xylanase activity from about 5000 U/g to about 8500 U/g.

4. The product according to claim 1, wherein the product has a glucanase activity from about 10000 U/g to about 18000 U/g.

5. The according to claim 1, wherein the product has a soluble arabinoxylan substrate to insoluble arabinoxylan substrate activity ratio (WE-AX/WU-AX) of less than about 7.0.

6. The product according to claim 1, wherein the product has a temperature optimum from about 40° C. to about 70° C.

7. The product according to claim 1, wherein the product comprises from about 200 to about 350 amino acids.

8. The product according to claim 1, wherein at least one of the first enzyme and the second enzyme comprises a signal peptide.

9. A brewing mash comprising:
   a first enzyme exhibiting endo-1,4-β-xylanase activity, said first enzyme having the amino acid sequence of SEQ ID NO:1;
   a second enzyme exhibiting endo-1,3(4)-β-glucanase activity, said second enzyme having the amino acid sequence of SEQ ID NO:7; and
   starch.

* * * * *

SEQUENCE LISTING

<160> NUMBER OF SEQ ID NOS: 18

<210> SEQ ID NO 1
<211> LENGTH: 302
<212> TYPE: PRT
<213> ORGANISM: Aspergillus tubigensis

<400> SEQUENCE: 1

Gln Ala Ser Val Ser Ile Asp Thr Lys Phe Lys Ala His Gly Lys Lys
1               5                   10                  15

-continued

Tyr Leu Gly Asn Ile Gly Asp Gln Tyr Thr Leu Thr Lys Asn Ser Lys
            20                  25                  30

Thr Pro Ala Ile Ile Lys Ala Asp Phe Gly Ala Leu Thr Pro Glu Asn
        35                  40                  45

Ser Met Lys Trp Asp Ala Thr Glu Pro Ser Arg Gly Gln Phe Ser Phe
 50                  55                  60

Ser Gly Ser Asp Tyr Leu Val Asn Phe Ala Gln Ser Asn Asn Lys Leu
65                   70                  75                  80

Ile Arg Gly His Thr Leu Val Trp His Ser Gln Leu Pro Ser Trp Val
                85                  90                  95

Gln Ala Ile Thr Asp Lys Asn Thr Leu Ile Glu Val Met Lys Asn His
            100                 105                 110

Ile Thr Thr Val Met Gln His Tyr Lys Gly Lys Ile Tyr Ala Trp Asp
        115                 120                 125

Val Val Asn Glu Ile Phe Asn Glu Asp Gly Ser Leu Arg Asp Ser Val
130                 135                 140

Phe Tyr Gln Val Ile Gly Glu Asp Tyr Val Arg Ile Ala Phe Glu Thr
145                 150                 155                 160

Ala Arg Ala Ala Asp Pro Asn Ala Lys Leu Tyr Ile Asn Asp Tyr Asn
                165                 170                 175

Leu Asp Ser Ala Ser Tyr Pro Lys Leu Thr Gly Met Val Ser His Val
            180                 185                 190

Lys Lys Trp Ile Glu Ala Gly Ile Pro Ile Asp Gly Ile Gly Ser Gln
        195                 200                 205

Thr His Leu Ser Ala Gly Gly Ala Gly Ile Ser Gly Ala Leu Asn
            210                 215                 220

Ala Leu Ala Gly Ala Gly Thr Lys Glu Ile Ala Val Thr Glu Leu Asp
225                 230                 235                 240

Ile Ala Gly Ala Ser Ser Thr Asp Tyr Val Glu Val Val Glu Ala Cys
                245                 250                 255

Leu Asp Gln Pro Lys Cys Ile Gly Ile Thr Val Trp Gly Val Ala Asp
            260                 265                 270

Pro Asp Ser Trp Arg Ser Ser Thr Pro Leu Leu Phe Asp Ser Asn
        275                 280                 285

Tyr Asn Pro Lys Pro Ala Tyr Thr Ala Ile Ala Asn Ala Leu
    290                 295                 300

<210> SEQ ID NO 2
<211> LENGTH: 386
<212> TYPE: PRT
<213> ORGANISM: Geosmithia emersonii

<400> SEQUENCE: 2

Ala Gly Leu Asn Thr Ala Ala Lys Ala Ile Gly Leu Lys Tyr Phe Gly
1               5                   10                  15

Thr Ala Thr Asp Asn Pro Glu Leu Ser Asp Thr Ala Tyr Glu Thr Gln
            20                  25                  30

Leu Asn Asn Thr Gln Asp Phe Gly Gln Leu Thr Pro Ala Asn Ser Met
        35                  40                  45

Lys Trp Asp Ala Thr Glu Pro Glu Gln Asn Val Phe Thr Phe Ser Ala
    50                  55                  60

Gly Asp Gln Ile Ala Asn Leu Ala Lys Ala Asn Gly Gln Met Leu Arg
65                  70                  75                  80

Cys His Asn Leu Val Trp Tyr Asn Gln Leu Pro Ser Trp Val Thr Ser

```
                        85                  90                  95
Gly Ser Trp Thr Asn Glu Thr Leu Leu Ala Ala Met Lys Asn His Ile
            100                 105                 110

Thr Asn Val Val Thr His Tyr Lys Gly Gln Cys Tyr Ala Trp Asp Val
            115                 120                 125

Val Asn Glu Ala Leu Asn Asp Asp Gly Thr Tyr Arg Ser Asn Val Phe
130                 135                 140

Tyr Gln Tyr Ile Gly Glu Ala Tyr Ile Pro Ile Ala Phe Ala Thr Ala
145                 150                 155                 160

Ala Ala Ala Asp Pro Asn Ala Lys Leu Tyr Tyr Asn Asp Tyr Asn Ile
                165                 170                 175

Glu Tyr Pro Gly Ala Lys Ala Thr Ala Ala Gln Asn Leu Val Lys Leu
            180                 185                 190

Val Gln Ser Tyr Gly Ala Arg Ile Asp Gly Val Gly Leu Gln Ser His
            195                 200                 205

Phe Ile Val Gly Glu Thr Pro Ser Thr Ser Ser Gln Gln Gln Asn Met
210                 215                 220

Ala Ala Phe Thr Ala Leu Gly Val Glu Val Ala Ile Thr Glu Leu Asp
225                 230                 235                 240

Ile Arg Met Gln Leu Pro Glu Thr Glu Ala Leu Leu Thr Gln Gln Ala
                245                 250                 255

Thr Asp Tyr Gln Ser Thr Val Gln Ala Cys Ala Asn Thr Lys Gly Cys
            260                 265                 270

Val Gly Ile Thr Val Trp Asp Trp Thr Asp Lys Tyr Ser Trp Val Pro
            275                 280                 285

Ser Thr Phe Ser Gly Tyr Gly Asp Ala Cys Pro Trp Asp Ala Asn Tyr
290                 295                 300

Gln Lys Lys Pro Ala Tyr Glu Gly Ile Leu Thr Gly Leu Gly Gln Thr
305                 310                 315                 320

Val Thr Ser Thr Thr Tyr Ile Ile Ser Pro Thr Thr Ser Val Gly Thr
                325                 330                 335

Gly Thr Thr Thr Ser Ser Gly Ser Gly Gly Thr Thr Gly Val Ala
            340                 345                 350

Gln His Trp Glu Gln Cys Gly Gly Leu Gly Trp Thr Gly Pro Thr Val
            355                 360                 365

Cys Ala Ser Gly Tyr Thr Cys Thr Val Ile Asn Glu Tyr Tyr Ser Gln
    370                 375                 380

Cys Leu
385

<210> SEQ ID NO 3
<211> LENGTH: 308
<212> TYPE: PRT
<213> ORGANISM: Aspergillus tubigensis

<400> SEQUENCE: 3

Glu Pro Ile Glu Pro Arg Gln Ala Ser Val Ser Ile Asp Thr Lys Phe
1               5                   10                  15

Lys Ala His Gly Lys Lys Tyr Leu Gly Asn Ile Gly Asp Gln Tyr Thr
            20                  25                  30

Leu Thr Lys Asn Ser Lys Thr Pro Ala Ile Ile Lys Ala Asp Phe Gly
        35                  40                  45

Ala Leu Thr Pro Glu Asn Ser Met Lys Trp Asp Ala Thr Glu Pro Ser
50                  55                  60
```

Arg Gly Gln Phe Ser Phe Gly Ser Asp Tyr Leu Val Asn Phe Ala
 65                  70                  75                  80

Gln Ser Asn Asn Lys Leu Ile Arg Gly His Thr Leu Val Trp His Ser
                 85                  90                  95

Gln Leu Pro Ser Trp Val Gln Ser Ile Thr Asp Lys Asn Thr Leu Ile
            100                 105                 110

Glu Val Met Lys Asn His Ile Thr Thr Val Met Gln His Tyr Lys Gly
        115                 120                 125

Lys Ile Tyr Ala Trp Asp Val Val Asn Glu Ile Phe Asn Glu Asp Gly
130                 135                 140

Ser Leu Arg Asp Ser Val Phe Tyr Lys Val Ile Gly Glu Asp Tyr Val
145                 150                 155                 160

Arg Ile Ala Phe Glu Thr Ala Arg Ala Ala Asp Pro Asn Ala Lys Leu
                165                 170                 175

Tyr Ile Asn Asp Tyr Asn Leu Asp Ser Ala Ser Tyr Pro Lys Leu Thr
            180                 185                 190

Gly Met Val Ser His Val Lys Lys Trp Ile Ala Ala Gly Ile Pro Ile
        195                 200                 205

Asp Gly Ile Gly Ser Gln Thr His Leu Ser Ala Gly Gly Ala Gly
210                 215                 220

Ile Ser Gly Ala Leu Asn Ala Leu Ala Gly Ala Gly Thr Lys Glu Ile
225                 230                 235                 240

Ala Val Thr Glu Leu Asp Ile Ala Gly Ala Ser Ser Thr Asp Tyr Val
                245                 250                 255

Glu Val Val Glu Ala Cys Leu Asn Gln Pro Lys Cys Ile Gly Ile Thr
            260                 265                 270

Val Trp Gly Val Ala Asp Pro Asp Ser Trp Arg Ser Ser Thr Pro
        275                 280                 285

Leu Leu Phe Asp Ser Asn Tyr Asn Pro Lys Pro Ala Tyr Thr Ala Ile
290                 295                 300

Ala Asn Ala Leu
305

<210> SEQ ID NO 4
<211> LENGTH: 406
<212> TYPE: PRT
<213> ORGANISM: Aspergillus aculeatus

<400> SEQUENCE: 4

Met Val Gly Leu Leu Ser Ile Thr Ala Ala Leu Ala Ala Thr Val Leu
1               5                   10                  15

Pro Asn Ile Val Ser Ala Val Gly Leu Asp Gln Ala Ala Val Ala Lys
            20                  25                  30

Gly Leu Gln Tyr Phe Gly Thr Ala Thr Asp Asn Pro Glu Leu Thr Asp
        35                  40                  45

Ile Pro Tyr Val Thr Gln Leu Asn Asn Thr Ala Asp Phe Gly Gln Ile
    50                  55                  60

Thr Pro Gly Asn Ser Met Lys Trp Asp Ala Thr Glu Pro Ser Gln Gly
65                  70                  75                  80

Thr Phe Thr Phe Thr Lys Gly Asp Val Ile Ala Asp Leu Ala Glu Gly
                85                  90                  95

Asn Gly Gln Tyr Leu Arg Cys His Thr Leu Val Trp Tyr Asn Gln Leu
            100                 105                 110

Pro Ser Trp Val Thr Ser Gly Thr Trp Thr Asn Ala Thr Leu Thr Ala
        115                 120                 125

```
Ala Leu Lys Asn His Ile Thr Asn Val Val Ser His Tyr Lys Gly Lys
        130                 135                 140

Cys Leu His Trp Asp Val Val Asn Glu Ala Leu Asn Asp Asp Gly Thr
145                 150                 155                 160

Tyr Arg Thr Asn Ile Phe Tyr Thr Thr Ile Gly Glu Ala Tyr Ile Pro
                165                 170                 175

Ile Ala Phe Ala Ala Ala Ala Ala Asp Pro Asp Ala Lys Leu Phe
            180                 185                 190

Tyr Asn Asp Tyr Asn Leu Glu Tyr Gly Gly Ala Lys Ala Ala Ser Ala
        195                 200                 205

Arg Ala Ile Val Gln Leu Val Lys Asn Ala Gly Ala Lys Ile Asp Gly
    210                 215                 220

Val Gly Leu Gln Ala His Phe Ser Val Gly Thr Val Pro Ser Thr Ser
225                 230                 235                 240

Ser Leu Val Ser Val Leu Gln Ser Phe Thr Ala Leu Gly Val Glu Val
                245                 250                 255

Ala Tyr Thr Glu Ala Asp Val Arg Ile Leu Leu Pro Thr Thr Ala Thr
            260                 265                 270

Thr Leu Ala Gln Gln Ser Ser Asp Phe Gln Ala Leu Val Gln Ser Cys
        275                 280                 285

Val Gln Thr Thr Gly Cys Val Gly Phe Thr Ile Trp Asp Trp Thr Asp
    290                 295                 300

Lys Tyr Ser Trp Val Pro Ser Thr Phe Ser Gly Tyr Gly Ala Ala Leu
305                 310                 315                 320

Pro Trp Asp Glu Asn Leu Val Lys Lys Pro Ala Tyr Asn Gly Leu Leu
                325                 330                 335

Ala Gly Met Gly Val Thr Val Thr Thr Thr Thr Thr Thr Thr Thr Ala
            340                 345                 350

Thr Ala Thr Gly Lys Thr Thr Thr Thr Thr Thr Gly Ala Thr Ser Thr
        355                 360                 365

Gly Thr Thr Ala Ala His Trp Gly Gln Cys Gly Gly Leu Asn Trp Ser
    370                 375                 380

Gly Pro Thr Ala Cys Ala Thr Gly Tyr Thr Cys Thr Tyr Val Asn Asp
385                 390                 395                 400

Tyr Tyr Ser Gln Cys Leu
                405

<210> SEQ ID NO 5
<211> LENGTH: 347
<212> TYPE: PRT
<213> ORGANISM: Trichoderma reesei

<400> SEQUENCE: 5

Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
                20                  25                  30

Ala Asn Leu Thr Glu Arg Thr Ala Asp Leu Trp Asp Arg Gln Ala Ser
            35                  40                  45

Gln Ser Ile Asp Gln Leu Ile Lys Arg Lys Gly Lys Leu Tyr Phe Gly
        50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
```

```
                         85                   90                   95
Gln Ser Leu Glu Asn Asn Gln Gly Gln Leu Asn Trp Gly Asp Ala Asp
                100                 105                 110

Tyr Leu Val Asn Phe Ala Gln Asn Gly Lys Ser Ile Arg Gly His
                115                 120                 125

Thr Leu Ile Trp His Ser Gln Leu Pro Ala Trp Val Asn Asn Ile Asn
            130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
                180                 185                 190

Leu Gly Glu Glu Phe Val Ser Ile Ala Phe Arg Ala Ala Arg Asp Ala
                195                 200                 205

Asp Pro Ser Ala Arg Leu Tyr Ile Asn Asp Tyr Asn Leu Asp Arg Ala
            210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
                260                 265                 270

Val Pro Val Thr Glu Leu Ala Ile Thr Glu Leu Asp Ile Gln Gly Ala
            275                 280                 285

Pro Thr Thr Asp Tyr Thr Gln Val Val Gln Ala Cys Leu Ser Val Ser
            290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
                340                 345

<210> SEQ ID NO 6
<211> LENGTH: 191
<212> TYPE: PRT
<213> ORGANISM: Trichoderma reesei

<400> SEQUENCE: 6

Gln Cys Ile Gln Pro Gly Thr Gly Tyr Asn Asn Gly Tyr Phe Tyr Ser
1               5                   10                  15

Tyr Trp Asn Asp Gly His Gly Gly Val Thr Tyr Cys Asn Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Arg Val Ile Asn Phe Ser Gly
        50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
                100                 105                 110
```

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
            165                 170                 175

Glu Gly Tyr Phe Ser Ser Gly Ser Ala Ser Ile Thr Val Ser Asp
            180                 185                 190

<210> SEQ ID NO 7
<211> LENGTH: 214
<212> TYPE: PRT
<213> ORGANISM: Bacillus subtilis

<400> SEQUENCE: 7

Gln Thr Gly Gly Ser Phe Phe Asp Pro Phe Asn Gly Tyr Asn Ser Gly
1               5                   10                  15

Phe Trp Gln Lys Ala Asp Gly Tyr Ser Asn Gly Asn Met Phe Asn Cys
            20                  25                  30

Thr Trp Arg Ala Asn Asn Val Ser Met Thr Ser Leu Gly Glu Met Arg
        35                  40                  45

Leu Ala Leu Thr Ser Pro Ala Tyr Asn Lys Phe Asp Cys Gly Glu Asn
50                  55                  60

Arg Ser Val Gln Thr Tyr Gly Tyr Gly Leu Tyr Glu Val Arg Met Lys
65                  70                  75                  80

Pro Ala Lys Asn Thr Gly Ile Val Ser Ser Phe Phe Thr Tyr Thr Gly
                85                  90                  95

Pro Thr Asp Gly Thr Pro Trp Asp Glu Ile Asp Ile Glu Phe Leu Gly
            100                 105                 110

Lys Asp Thr Thr Lys Val Gln Phe Asn Tyr Tyr Thr Asn Gly Ala Gly
            115                 120                 125

Asn His Glu Lys Ile Val Asp Leu Gly Phe Asp Ala Ala Asn Ala Tyr
    130                 135                 140

His Thr Tyr Ala Phe Asp Trp Gln Pro Asn Ser Ile Lys Trp Tyr Val
145                 150                 155                 160

Asp Gly Gln Leu Lys His Thr Ala Thr Asn Gln Ile Pro Thr Thr Pro
            165                 170                 175

Gly Lys Ile Met Met Asn Leu Trp Asn Gly Thr Gly Val Asp Glu Trp
            180                 185                 190

Leu Gly Ser Tyr Asn Gly Val Asn Pro Leu Tyr Ala His Tyr Asp Trp
            195                 200                 205

Val Arg Tyr Thr Lys Lys
            210

<210> SEQ ID NO 8
<211> LENGTH: 316
<212> TYPE: PRT
<213> ORGANISM: Geosmithia emersonii

<400> SEQUENCE: 8

Ala Pro Val Lys Glu Lys Gly Ile Lys Lys Arg Ala Ser Pro Phe Gln
1               5                   10                  15

Trp Phe Gly Ser Asn Glu Ser Gly Ala Glu Phe Gly Asn Asn Asn Ile
            20                  25                  30

Pro Gly Val Glu Gly Thr Asp Tyr Thr Phe Pro Asn Thr Ser Ala Ile
            35                  40                  45

Gln Ile Leu Ile Asp Gln Gly Met Asn Ile Phe Arg Val Pro Phe Leu
 50                  55                  60

Met Glu Arg Met Val Pro Asn Gln Met Thr Gly Pro Val Asp Ser Ala
 65                  70                  75                  80

Tyr Phe Gln Gly Tyr Ser Gln Val Ile Asn Tyr Ile Thr Ser His Gly
                 85                  90                  95

Ala Ser Ala Val Ile Asp Pro His Asn Phe Gly Arg Tyr Tyr Asn Asn
            100                 105                 110

Ile Ile Ser Ser Pro Ser Asp Phe Gln Thr Phe Trp His Thr Ile Ala
            115                 120                 125

Ser Asn Phe Ala Asp Asn Asp Asn Val Ile Phe Asp Thr Asn Asn Glu
 130                 135                 140

Tyr His Asp Met Asp Glu Ser Leu Val Val Gln Leu Asn Gln Ala Ala
145                 150                 155                 160

Ile Asp Gly Ile Arg Ala Ala Gly Ala Thr Ser Gln Tyr Ile Phe Val
                165                 170                 175

Glu Gly Asn Ser Trp Thr Gly Ala Trp Thr Trp Thr Gln Val Asn Asp
            180                 185                 190

Ala Met Ala Asn Leu Thr Asp Pro Gln Asn Lys Ile Val Tyr Glu Met
            195                 200                 205

His Gln Tyr Leu Asp Ser Asp Gly Ser Gly Thr Ser Asp Gln Cys Val
            210                 215                 220

Asn Ser Thr Ile Gly Gln Asp Arg Val Glu Ser Ala Thr Ala Trp Leu
225                 230                 235                 240

Lys Gln Asn Gly Lys Lys Ala Ile Leu Gly Glu Tyr Ala Gly Gly Ala
                245                 250                 255

Asn Ser Val Cys Glu Thr Ala Val Thr Gly Met Leu Asp Tyr Leu Ala
            260                 265                 270

Asn Asn Thr Asp Val Trp Thr Gly Ala Ile Trp Trp Ala Ala Gly Pro
            275                 280                 285

Trp Trp Gly Asp Tyr Ile Phe Ser Met Glu Pro Pro Ser Gly Ile Ala
290                 295                 300

Tyr Glu Gln Val Leu Pro Leu Leu Gln Pro Tyr Leu
305                 310                 315

<210> SEQ ID NO 9
<211> LENGTH: 441
<212> TYPE: PRT
<213> ORGANISM: Bacillus subtilis

<400> SEQUENCE: 9

Asp Asp Tyr Ser Val Val Glu Glu His Gly Gln Leu Ser Ile Ser Asn
 1               5                  10                  15

Gly Glu Leu Val Asn Glu Arg Gly Glu Gln Val Gln Leu Lys Gly Met
            20                  25                  30

Ser Ser His Gly Leu Gln Trp Tyr Gly Gln Phe Val Asn Tyr Glu Ser
            35                  40                  45

Met Lys Trp Leu Arg Asp Asp Trp Gly Ile Thr Val Phe Arg Ala Ala
 50                  55                  60

Met Tyr Thr Ser Ser Gly Gly Tyr Ile Asp Asp Pro Ser Val Lys Glu
 65                  70                  75                  80

Lys Val Lys Glu Thr Val Glu Ala Ala Ile Asp Leu Gly Ile Tyr Val
                 85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
            115                 120                 125

Tyr Pro Asn Val Ile Tyr Glu Ile Ala Asn Glu Pro Asn Gly Ser Asp
130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
            195                 200                 205

Asn Leu Arg Asp Gln Val Asp Tyr Ala Leu Asp Gln Gly Ala Ala Ile
            210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
            245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
            275                 280                 285

Leu Ser Pro Ser Gly Thr Phe Val Arg Glu Lys Ile Arg Glu Ser Ala
            290                 295                 300

Ser Ile Pro Pro Ser Asp Pro Thr Pro Ser Asp Pro Gly Glu Pro
305                 310                 315                 320

Asp Pro Gly Glu Pro Asp Pro Thr Pro Ser Asp Pro Gly Glu Tyr
            325                 330                 335

Pro Ala Trp Asp Ser Asn Gln Ile Tyr Thr Asn Glu Ile Val Tyr His
            340                 345                 350

Asn Gly Gln Leu Trp Gln Ala Lys Trp Trp Thr Gln Asn Gln Glu Pro
            355                 360                 365

Gly Asp Pro Tyr Gly Pro Trp Glu Pro Leu Lys Ser Asp Pro Asp Ser
370                 375                 380

Gly Glu Pro Asp Pro Thr Pro Pro Ser Asp Pro Gly Glu Tyr Pro Ala
385                 390                 395                 400

Trp Asp Ser Asn Gln Ile Tyr Thr Asn Glu Ile Val Tyr His Asn Gly
                405                 410                 415

Gln Leu Trp Gln Ala Lys Trp Trp Thr Gln Asn Gln Glu Pro Gly Asp
            420                 425                 430

Pro Tyr Gly Pro Trp Glu Pro Leu Asn
        435                 440

<210> SEQ ID NO 10
<211> LENGTH: 397
<212> TYPE: PRT
<213> ORGANISM: Trichoderma reesei

<400> SEQUENCE: 10

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr

```
            20                  25                  30
Ala Gln Cys Ile Pro Gly Ala Thr Thr Ile Thr Thr Ser Thr Arg Pro
        35                  40                  45

Pro Ser Gly Pro Thr Thr Thr Arg Ala Thr Ser Thr Ser Ser Ser
50                  55                  60

Thr Pro Pro Thr Ser Ser Gly Val Arg Phe Ala Gly Val Asn Ile Ala
65                  70                  75                  80

Gly Phe Asp Phe Gly Cys Thr Thr Asp Gly Thr Cys Val Thr Ser Lys
                85                  90                  95

Val Tyr Pro Pro Leu Lys Asn Phe Thr Gly Ser Asn Asn Tyr Pro Asp
            100                 105                 110

Gly Ile Gly Gln Met Gln His Phe Val Asn Asp Asp Gly Met Thr Ile
        115                 120                 125

Phe Arg Leu Pro Val Gly Trp Gln Tyr Leu Val Asn Asn Asn Leu Gly
    130                 135                 140

Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Gly Ile Ile Gly Gln Gly Gly Pro Thr Asn Ala
            180                 185                 190

Gln Phe Thr Ser Leu Trp Ser Gln Leu Ala Ser Lys Tyr Ala Ser Gln
        195                 200                 205

Ser Arg Val Trp Phe Gly Ile Met Asn Glu Pro His Asp Val Asn Ile
    210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
                245                 250                 255

Ser Ala Gly Ala Phe Ile Ser Asp Gly Ser Ala Ala Ala Leu Ser Gln
            260                 265                 270

Val Thr Asn Pro Asp Gly Ser Thr Thr Asn Leu Ile Phe Asp Val His
        275                 280                 285

Lys Tyr Leu Asp Ser Asp Asn Ser Gly Thr His Ala Glu Cys Thr Thr
    290                 295                 300

Asn Asn Ile Asp Gly Ala Phe Ser Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Met Cys Gln Gln Ile Gln Tyr Leu Asn Gln Asn
            340                 345                 350

Ser Asp Val Tyr Leu Gly Tyr Val Gly Trp Gly Ala Gly Ser Phe Asp
        355                 360                 365

Ser Thr Tyr Val Leu Thr Glu Thr Pro Thr Gly Ser Gly Asn Ser Trp
    370                 375                 380

Thr Asp Thr Ser Leu Val Ser Ser Cys Leu Ala Arg Lys
385                 390                 395

<210> SEQ ID NO 11
<211> LENGTH: 218
<212> TYPE: PRT
<213> ORGANISM: Trichoderma reesei

<400> SEQUENCE: 11
```

```
Gln Thr Ser Cys Asp Gln Trp Ala Thr Phe Thr Gly Asn Gly Tyr Thr
1               5                   10                  15

Val Ser Asn Asn Leu Trp Gly Ala Ser Ala Gly Ser Gly Phe Gly Cys
            20                  25                  30

Val Thr Ala Val Ser Leu Ser Gly Gly Ala Ser Trp His Ala Asp Trp
        35                  40                  45

Gln Trp Ser Gly Gly Gln Asn Asn Val Lys Ser Tyr Gln Asn Ser Gln
    50                  55                  60

Ile Ala Ile Pro Gln Lys Arg Thr Val Asn Ser Ile Ser Met Pro
65                  70                  75                  80

Thr Thr Ala Ser Trp Ser Tyr Ser Gly Ser Asn Ile Arg Ala Asn Val
                85                  90                  95

Ala Tyr Asp Leu Phe Thr Ala Ala Asn Pro Asn His Val Thr Tyr Ser
            100                 105                 110

Gly Asp Tyr Glu Leu Met Ile Trp Leu Gly Lys Tyr Gly Asp Ile Gly
        115                 120                 125

Pro Ile Gly Ser Ser Gln Gly Thr Val Asn Val Gly Gly Gln Ser Trp
    130                 135                 140

Thr Leu Tyr Tyr Gly Tyr Asn Gly Ala Met Gln Val Tyr Ser Phe Val
145                 150                 155                 160

Ala Gln Thr Asn Thr Thr Asn Tyr Ser Gly Asp Val Lys Asn Phe Phe
                165                 170                 175

Asn Tyr Leu Arg Asp Asn Lys Gly Tyr Asn Ala Ala Gly Gln Tyr Val
            180                 185                 190

Leu Ser Tyr Gln Phe Gly Thr Glu Pro Phe Thr Gly Ser Gly Thr Leu
        195                 200                 205

Asn Val Ala Ser Trp Thr Ala Ser Ile Asn
    210                 215

<210> SEQ ID NO 12
<211> LENGTH: 322
<212> TYPE: PRT
<213> ORGANISM: Trichoderma reesei

<400> SEQUENCE: 12

His Gly His Ile Asn Asp Ile Val Ile Asn Gly Val Trp Tyr Gln Ala
1               5                   10                  15

Tyr Asp Pro Thr Thr Phe Pro Tyr Glu Ser Asn Pro Pro Ile Val Val
            20                  25                  30

Gly Trp Thr Ala Ala Asp Leu Asp Asn Gly Phe Val Ser Pro Asp Ala
        35                  40                  45

Tyr Gln Asn Pro Asp Ile Ile Cys His Lys Asn Ala Thr Asn Ala Lys
    50                  55                  60

Gly His Ala Ser Val Lys Ala Gly Asp Thr Ile Leu Phe Gln Trp Val
65                  70                  75                  80

Pro Val Pro Trp Pro His Pro Gly Pro Ile Val Asp Tyr Leu Ala Asn
                85                  90                  95

Cys Asn Gly Asp Cys Glu Thr Val Asp Lys Thr Thr Leu Glu Phe Phe
            100                 105                 110

Lys Ile Asp Gly Val Gly Leu Leu Ser Gly Gly Asp Pro Gly Thr Trp
        115                 120                 125

Ala Ser Asp Val Leu Ile Ser Asn Asn Thr Trp Val Val Lys Ile
    130                 135                 140

Pro Asp Asn Leu Ala Pro Gly Asn Tyr Val Leu Arg His Glu Ile Ile
145                 150                 155                 160
```

```
Ala Leu His Ser Ala Gly Gln Ala Asn Gly Ala Gln Asn Tyr Pro Gln
                165                 170                 175

Cys Phe Asn Ile Ala Val Ser Gly Gly Ser Leu Gln Pro Ser Gly
            180                 185                 190

Val Leu Gly Thr Asp Leu Tyr His Ala Thr Asp Pro Gly Val Leu Ile
            195                 200                 205

Asn Ile Tyr Thr Ser Pro Leu Asn Tyr Ile Ile Pro Gly Pro Thr Val
        210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly Gly Ser Gly Pro Thr Ser
            245                 250                 255

Arg Thr Thr Thr Thr Ala Arg Thr Thr Gln Ala Ser Ser Arg Pro Ser
            260                 265                 270

Ser Thr Pro Pro Ala Thr Thr Ser Ala Pro Ala Gly Gly Pro Thr Gln
        275                 280                 285

Thr Leu Tyr Gly Gln Cys Gly Gly Ser Gly Tyr Ser Gly Pro Thr Arg
        290                 295                 300

Cys Ala Pro Pro Ala Thr Cys Ser Thr Asn Pro Tyr Tyr Ala Gln Cys
305                 310                 315                 320

Leu Asn

<210> SEQ ID NO 13
<211> LENGTH: 761
<212> TYPE: PRT
<213> ORGANISM: Trichoderma reesei

<400> SEQUENCE: 13

Ala Phe Ser Trp Lys Asn Val Lys Leu Gly Gly Gly Gly Phe Val
1               5                   10                  15

Pro Gly Ile Ile Phe His Pro Lys Thr Lys Gly Val Ala Tyr Ala Arg
            20                  25                  30

Thr Asp Ile Gly Gly Leu Tyr Arg Leu Asn Ala Asp Asp Ser Trp Thr
        35                  40                  45

Ala Val Thr Asp Gly Ile Ala Asp Asn Ala Gly Trp His Asn Trp Gly
    50                  55                  60

Ile Asp Ala Val Ala Leu Asp Pro Gln Asp Asp Gln Lys Val Tyr Ala
65                  70                  75                  80

Ala Val Gly Met Tyr Thr Asn Ser Trp Asp Pro Ser Asn Gly Ala Ile
                85                  90                  95

Ile Arg Ser Ser Asp Arg Gly Ala Thr Trp Ser Phe Thr Asn Leu Pro
            100                 105                 110

Phe Lys Val Gly Gly Asn Met Pro Gly Arg Gly Ala Gly Glu Arg Leu
        115                 120                 125

Ala Val Asp Pro Ala Asn Ser Asn Ile Ile Tyr Phe Gly Ala Arg Ser
    130                 135                 140

Gly Asn Gly Leu Trp Lys Ser Thr Asp Gly Gly Val Thr Phe Ser Lys
145                 150                 155                 160

Val Ser Ser Phe Thr Ala Thr Gly Thr Tyr Ile Pro Asp Pro Ser Asp
                165                 170                 175

Ser Asn Gly Tyr Asn Ser Asp Lys Gln Gly Leu Met Trp Val Thr Phe
            180                 185                 190

Asp Ser Thr Ser Ser Thr Thr Gly Gly Ala Thr Ser Arg Ile Phe Val
        195                 200                 205
```

-continued

Gly Thr Ala Asp Asn Ile Thr Ala Ser Val Tyr Val Ser Thr Asn Ala
210                 215                 220

Gly Ser Thr Trp Ser Ala Val Pro Gly Gln Pro Gly Lys Tyr Phe Pro
225                 230                 235                 240

His Lys Ala Lys Leu Gln Pro Ala Glu Lys Ala Leu Tyr Leu Thr Tyr
            245                 250                 255

Ser Trp Trp Pro Asp Ala Gln Leu Phe Arg Ser Thr Asp Ser Gly Thr
            260                 265                 270

Thr Trp Ser Pro Ile Trp Ala Trp Ala Ser Tyr Pro Thr Glu Thr Tyr
        275                 280                 285

Tyr Tyr Ser Ile Ser Thr Pro Lys Ala Pro Trp Ile Lys Asn Asn Phe
        290                 295                 300

Ile Asp Val Thr Ser Glu Ser Pro Ser Asp Gly Leu Ile Lys Arg Leu
305                 310                 315                 320

Gly Trp Met Ile Glu Ser Leu Glu Ile Asp Pro Thr Asp Ser Asn His
                325                 330                 335

Trp Leu Tyr Gly Thr Gly Met Thr Ile Phe Gly Gly His Asp Leu Thr
                340                 345                 350

Asn Trp Asp Thr Arg His Asn Val Ser Ile Gln Ser Leu Ala Asp Gly
            355                 360                 365

Ile Glu Glu Phe Ser Val Gln Asp Leu Ala Ser Ala Pro Gly Gly Ser
370                 375                 380

Glu Leu Leu Ala Ala Val Gly Asp Asp Asn Gly Phe Thr Phe Ala Ser
385                 390                 395                 400

Arg Asn Asp Leu Gly Thr Ser Pro Gln Thr Val Trp Ala Thr Pro Thr
                405                 410                 415

Trp Ala Thr Ser Thr Ser Val Asp Tyr Ala Gly Asn Ser Val Lys Ser
                420                 425                 430

Val Val Arg Val Gly Asn Thr Ala Gly Thr Gln Gln Val Ala Ile Ser
        435                 440                 445

Ser Asp Gly Gly Ala Thr Trp Ser Ile Asp Tyr Ala Ala Asp Thr Ser
    450                 455                 460

Met Asn Gly Gly Thr Val Ala Tyr Ser Ala Asp Gly Asp Thr Ile Leu
465                 470                 475                 480

Trp Ser Thr Ala Ser Ser Gly Val Gln Arg Ser Gln Phe Gln Gly Ser
                485                 490                 495

Phe Ala Ser Val Ser Ser Leu Pro Ala Gly Ala Val Ile Ala Ser Asp
                500                 505                 510

Lys Lys Thr Asn Ser Val Phe Tyr Ala Gly Ser Gly Ser Thr Phe Tyr
            515                 520                 525

Val Ser Lys Asp Thr Gly Ser Ser Phe Thr Arg Gly Pro Lys Leu Gly
530                 535                 540

Ser Ala Gly Thr Ile Arg Asp Ile Ala Ala His Pro Thr Thr Ala Gly
545                 550                 555                 560

Thr Leu Tyr Val Ser Thr Asp Val Gly Ile Phe Arg Ser Thr Asp Ser
                565                 570                 575

Gly Thr Thr Phe Gly Gln Val Ser Thr Ala Leu Thr Asn Thr Tyr Gln
                580                 585                 590

Ile Ala Leu Gly Val Gly Ser Gly Ser Asn Trp Asn Leu Tyr Ala Phe
            595                 600                 605

Gly Thr Gly Pro Ser Gly Ala Arg Leu Tyr Ala Ser Gly Asp Ser Gly
610                 615                 620

```
Ala Ser Trp Thr Asp Ile Gln Gly Ser Gln Gly Phe Gly Ser Ile Asp
625                 630                 635                 640

Ser Thr Lys Val Ala Gly Ser Gly Ser Thr Ala Gly Gln Val Tyr Val
            645                 650                 655

Gly Thr Asn Gly Arg Gly Val Phe Tyr Ala Gln Gly Thr Val Gly Gly
        660                 665                 670

Gly Thr Gly Gly Thr Ser Ser Thr Lys Gln Ser Ser Ser Ser Thr
        675                 680                 685

Ser Ser Ala Ser Ser Ser Thr Thr Leu Arg Ser Ser Val Val Ser Thr
        690                 695                 700

Thr Arg Ala Ser Thr Val Thr Ser Ser Arg Thr Ser Ser Ala Ala Gly
705                 710                 715                 720

Pro Thr Gly Ser Gly Val Ala Gly His Tyr Ala Gln Cys Gly Gly Ile
                725                 730                 735

Gly Trp Thr Gly Pro Thr Gln Cys Val Ala Pro Tyr Val Cys Gln Lys
                740                 745                 750

Gln Asn Asp Tyr Tyr Tyr Gln Cys Val
                755                 760

<210> SEQ ID NO 14
<211> LENGTH: 230
<212> TYPE: PRT
<213> ORGANISM: Trichoderma reesei

<400> SEQUENCE: 14

His Gly Gln Val Gln Asn Phe Thr Ile Asn Gly Gln Tyr Asn Gln Gly
1               5                   10                  15

Phe Ile Leu Asp Tyr Tyr Gln Lys Gln Asn Thr Gly His Phe Pro
                20                  25                  30

Asn Val Ala Gly Trp Tyr Ala Glu Asp Leu Asp Leu Gly Phe Ile Ser
            35                  40                  45

Pro Asp Gln Tyr Thr Thr Pro Asp Ile Val Cys His Lys Asn Ala Ala
    50                  55                  60

Pro Gly Ala Ile Ser Ala Thr Ala Ala Gly Ser Asn Ile Val Phe
65                  70                  75                  80

Gln Trp Gly Pro Gly Val Trp Pro His Pro Tyr Gly Pro Ile Val Thr
                85                  90                  95

Tyr Val Val Glu Cys Ser Gly Ser Cys Thr Thr Val Asn Lys Asn Asn
                100                 105                 110

Leu Arg Trp Val Lys Ile Gln Glu Ala Gly Ile Asn Tyr Asn Thr Gln
            115                 120                 125

Val Trp Ala Gln Gln Asp Leu Ile Asn Gln Gly Asn Lys Trp Thr Val
    130                 135                 140

Lys Ile Pro Ser Ser Leu Arg Pro Gly Asn Tyr Val Phe Arg His Glu
145                 150                 155                 160

Leu Leu Ala Ala His Gly Ala Ser Ser Ala Asn Gly Met Gln Asn Tyr
                165                 170                 175

Pro Gln Cys Val Asn Ile Ala Val Thr Gly Ser Gly Thr Lys Ala Leu
                180                 185                 190

Pro Ala Gly Thr Pro Ala Thr Gln Leu Tyr Lys Pro Thr Asp Pro Gly
            195                 200                 205

Ile Leu Phe Asn Pro Tyr Thr Thr Ile Thr Ser Tyr Thr Ile Pro Gly
    210                 215                 220

Pro Ala Leu Trp Gln Gly
225                 230
```

<210> SEQ ID NO 15
<211> LENGTH: 419
<212> TYPE: PRT
<213> ORGANISM: Trichoderma reesei

<400> SEQUENCE: 15

```
Gly Lys Ile Lys Tyr Leu Gly Val Ala Ile Pro Gly Ile Asp Phe Gly
 1               5                  10                  15

Cys Asp Ile Asp Gly Ser Cys Pro Thr Asp Thr Ser Ser Val Pro Leu
            20                  25                  30

Leu Ser Tyr Lys Gly Gly Asp Gly Ala Gly Gln Met Lys His Phe Ala
        35                  40                  45

Glu Asp Asp Gly Leu Asn Val Phe Arg Ile Ser Ala Thr Trp Gln Phe
50                  55                  60

Val Leu Asn Asn Thr Val Asp Gly Lys Leu Asp Glu Leu Asn Trp Gly
65                  70                  75                  80

Ser Tyr Asn Lys Val Val Asn Ala Cys Leu Glu Thr Gly Ala Tyr Cys
                85                  90                  95

Met Ile Asp Met His Asn Phe Ala Arg Tyr Asn Gly Gly Ile Ile Gly
            100                 105                 110

Gln Gly Gly Val Ser Asp Asp Ile Phe Val Asp Leu Trp Val Gln Ile
        115                 120                 125

Ala Lys Tyr Tyr Glu Asp Asn Asp Lys Ile Ile Phe Gly Leu Met Asn
130                 135                 140

Glu Pro His Asp Leu Asp Ile Glu Ile Trp Ala Gln Thr Cys Gln Lys
145                 150                 155                 160

Val Val Thr Ala Ile Arg Lys Ala Gly Ala Thr Ser Gln Met Ile Leu
                165                 170                 175

Leu Pro Gly Thr Asn Phe Ala Ser Val Glu Thr Tyr Val Ser Thr Gly
            180                 185                 190

Ser Ala Glu Ala Leu Gly Lys Ile Thr Asn Pro Asp Gly Ser Thr Asp
        195                 200                 205

Leu Leu Tyr Phe Asp Val His Lys Tyr Leu Asp Ile Asn Asn Ser Gly
210                 215                 220

Ser His Ala Glu Cys Thr Thr Asp Asn Val Asp Ala Phe Asn Asp Phe
225                 230                 235                 240

Ala Asp Trp Leu Arg Gln Asn Lys Arg Gln Ala Ile Ile Ser Glu Thr
                245                 250                 255

Gly Ala Ser Met Glu Pro Ser Cys Met Thr Ala Phe Cys Ala Gln Asn
            260                 265                 270

Lys Ala Ile Ser Glu Asn Ser Asp Val Tyr Ile Gly Phe Val Gly Trp
        275                 280                 285

Gly Ala Gly Ser Phe Asp Thr Ser Tyr Ile Leu Thr Leu Thr Pro Leu
290                 295                 300

Gly Lys Pro Gly Asn Tyr Thr Asp Asn Lys Leu Met Asn Glu Cys Ile
305                 310                 315                 320

Leu Asp Gln Phe Thr Leu Asp Glu Lys Tyr Arg Pro Thr Pro Thr Ser
                325                 330                 335

Ile Ser Thr Ala Ala Glu Glu Thr Thr Ala Thr Ala Thr Ala Ser Asp
            340                 345                 350

Gly Asp Ala Pro Ser Thr Thr Lys Pro Ile Phe Arg Glu Glu Thr Ala
        355                 360                 365

Ser Pro Thr Pro Asn Ala Val Thr Lys Pro Ser Pro Asp Thr Ser Asp
```

```
                 370                 375                 380
Ser Ser Asp Asp Asp Lys Asp Ser Ala Ala Ser Met Ser Ala Gln Gly
385                 390                 395                 400

Leu Thr Gly Thr Val Leu Phe Thr Val Ala Ala Leu Gly Tyr Met Leu
                405                 410                 415

Val Ala Phe

<210> SEQ ID NO 16
<211> LENGTH: 499
<212> TYPE: PRT
<213> ORGANISM: Bacillus subtilis

<400> SEQUENCE: 16

Met Lys Arg Ser Ile Ser Ile Phe Ile Thr Cys Leu Leu Ile Thr Leu
1               5                   10                  15

Leu Thr Met Gly Gly Met Ile Ala Ser Pro Ala Ser Ala Ala Gly Thr
                20                  25                  30

Lys Thr Pro Val Ala Lys Asn Gly Gln Leu Ser Ile Lys Gly Thr Gln
            35                  40                  45

Leu Val Asn Arg Asp Gly Lys Ala Val Gln Leu Lys Gly Ile Ser Ser
50                  55                  60

His Gly Leu Gln Trp Tyr Gly Glu Tyr Val Asn Lys Asp Ser Leu Lys
65                  70                  75                  80

Trp Leu Arg Asp Asp Trp Gly Ile Thr Val Phe Arg Ala Ala Met Tyr
                85                  90                  95

Thr Ala Asp Gly Gly Tyr Ile Asp Asn Pro Ser Val Lys Asn Lys Val
            100                 105                 110

Lys Glu Ala Val Glu Ala Ala Lys Glu Leu Gly Ile Tyr Val Ile Ile
        115                 120                 125

Asp Trp His Ile Leu Asn Asp Gly Asn Pro Asn Gln Asn Lys Glu Lys
130                 135                 140

Ala Lys Glu Phe Phe Lys Glu Met Ser Ser Leu Tyr Gly Asn Thr Pro
145                 150                 155                 160

Asn Val Ile Tyr Glu Ile Ala Asn Glu Pro Asn Gly Asp Val Asn Trp
                165                 170                 175

Lys Arg Asp Ile Lys Pro Tyr Ala Glu Glu Val Ile Ser Val Ile Arg
            180                 185                 190

Lys Asn Asp Pro Asp Asn Ile Ile Val Gly Thr Gly Thr Trp Ser
        195                 200                 205

Gln Asp Val Asn Asp Ala Ala Asp Asp Gln Leu Lys Asp Ala Asn Val
210                 215                 220

Met Tyr Ala Leu His Phe Tyr Ala Gly Thr His Gly Gln Phe Leu Arg
225                 230                 235                 240

Asp Lys Ala Asn Tyr Ala Leu Ser Lys Gly Ala Pro Ile Phe Val Thr
                245                 250                 255

Glu Trp Gly Thr Ser Asp Ala Ser Gly Asn Gly Gly Val Phe Leu Asp
            260                 265                 270

Gln Ser Arg Glu Trp Leu Lys Tyr Leu Asp Ser Lys Thr Ile Ser Trp
        275                 280                 285

Val Asn Trp Asn Leu Ser Asp Lys Gln Glu Ser Ser Ala Leu Lys
290                 295                 300

Pro Gly Ala Ser Lys Thr Gly Gly Trp Arg Leu Ser Asp Leu Ser Ala
305                 310                 315                 320

Ser Gly Thr Phe Val Arg Glu Asn Ile Leu Gly Thr Lys Asp Ser Thr
```

325                 330                 335
Lys Asp Ile Pro Glu Thr Pro Ser Lys Asp Lys Pro Thr Gln Glu Asn
            340                 345                 350

Gly Ile Ser Val Gln Tyr Arg Ala Gly Asp Gly Ser Met Asn Ser Asn
        355                 360                 365

Gln Ile Arg Pro Gln Leu Gln Ile Lys Asn Asn Gly Asn Thr Thr Val
    370                 375                 380

Asp Leu Lys Asp Val Thr Ala Arg Tyr Trp Tyr Lys Ala Lys Asn Lys
385                 390                 395                 400

Gly Gln Asn Phe Asp Cys Asp Tyr Ala Gln Ile Gly Cys Gly Asn Val
                405                 410                 415

Thr His Lys Phe Val Thr Leu His Lys Pro Lys Gln Gly Ala Asp Thr
            420                 425                 430

Tyr Leu Glu Leu Gly Phe Lys Asn Gly Thr Leu Ala Pro Gly Ala Ser
        435                 440                 445

Thr Gly Asn Ile Gln Leu Arg Leu His Asn Asp Asp Trp Ser Asn Tyr
    450                 455                 460

Ala Gln Ser Gly Asp Tyr Ser Phe Phe Lys Ser Asn Thr Phe Lys Thr
465                 470                 475                 480

Thr Lys Lys Ile Thr Leu Tyr Asp Gln Gly Lys Leu Ile Trp Gly Thr
                485                 490                 495

Glu Pro Asn

<210> SEQ ID NO 17
<211> LENGTH: 185
<212> TYPE: PRT
<213> ORGANISM: Artificial sequence
<220> FEATURE:
<223> OTHER INFORMATION: Bacillus subtilis xylanase variant

<400> SEQUENCE: 17

Ala Ser Thr Asp Tyr Trp Gln Asn Trp Thr Phe Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Asp Thr Thr Phe Thr Gln Tyr
        115                 120                 125

Trp Ser Val Arg Gln Ser Lys Arg Pro Thr Gly Ser Asn Ala Thr Ile
    130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

```
<210> SEQ ID NO 18
<211> LENGTH: 185
<212> TYPE: PRT
<213> ORGANISM: Artificial sequence
<220> FEATURE:
<223> OTHER INFORMATION: Bacillus subtilis xylanase variant

<400> SEQUENCE: 18

Ala Ser Thr Asp Tyr Trp Gln Asn Trp Thr Asp Gly Tyr Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Tyr Ser Asp Gly Gly Trp Tyr Asp Ile Tyr Thr Ala Thr Arg
            100                 105                 110

Asp Asn Ala Pro Ser Ile Asp Gly Asp Phe Thr Thr Phe Thr Gln Tyr
        115                 120                 125

Trp Ser Val Arg Gln Ser Lys Arg Pro Thr Gly Ser Asn Ala Thr Ile
    130                 135                 140

Thr Phe Ser Asn His Val Asn Ala Trp Arg Ser His Gly Met Asp Leu
145                 150                 155                 160

Gly Ser Asn Trp Ala Tyr Gln Val Met Ala Thr Glu Gly Tyr Leu Ser
                165                 170                 175

Ser Gly Ser Ser Asn Val Thr Val Trp
            180                 185
```